US011819580B2

(12) United States Patent
Bettilyon et al.

(10) Patent No.: US 11,819,580 B2
(45) Date of Patent: Nov. 21, 2023

(54) METHOD OF CHEMICALLY DISINFECTING A VEHICLE

(71) Applicant: PurWorld Technologies LLC, Dallas, TX (US)

(72) Inventors: Allen K. Bettilyon, Dallas, TX (US); Robert Adams, Austin, TX (US)

(73) Assignee: PurWorld Technologies LLC, Dallas, TX (US)

( * ) Notice: Subject to any disclaimer, the term of this patent is extended or adjusted under 35 U.S.C. 154(b) by 375 days.

(21) Appl. No.: 16/948,428

(22) Filed: Sep. 17, 2020

(65) Prior Publication Data

US 2020/0405894 A1 Dec. 31, 2020

Related U.S. Application Data

(63) Continuation-in-part of application No. 15/787,650, filed on Oct. 18, 2017, now Pat. No. 10,800,664.

(Continued)

(51) Int. Cl.
*A61L 2/08* (2006.01)
*G05B 19/4155* (2006.01)
*A61L 2/10* (2006.01)
*A61L 2/22* (2006.01)
*A61L 2/28* (2006.01)
(Continued)

(52) U.S. Cl.
CPC ............. *A61L 2/088* (2013.01); *A61L 2/10* (2013.01); *A61L 2/22* (2013.01); *A61L 2/28* (2013.01); *G05B 19/4155* (2013.01); *A61L 2101/02* (2020.08); *A61L 2101/34* (2020.08);
(Continued)

(58) Field of Classification Search
CPC ... A61L 2/088; A61L 2/10; A61L 2/22; A61L 2/28; A61L 9/14; A61L 2202/14; A61L 2202/16; A61L 2101/02; A61L 2101/34; A61L 2202/15; A61L 2202/25;
(Continued)

(56) References Cited

U.S. PATENT DOCUMENTS 6,754,570 B2    6/2004    Iihoshi et al.
6,905,814 B1    6/2005    Aubay et al.
(Continued)

FOREIGN PATENT DOCUMENTS

CN    104357223 A    2/2015
CN    209738761      12/2019
(Continued)

OTHER PUBLICATIONS

"Driverpure FAQ's: How does DrivePur work?," DrivePur®, drivepur.com, Aug. 5, 2016. https://web.archive.org/web/20160805223941/http://www.drivepur.com/become-a--drivepur-certified-dealership/.
(Continued)

*Primary Examiner* — Regina M Yoo
(74) *Attorney, Agent, or Firm* — Schultz & Associates, P.C.

(57) ABSTRACT

A chemical disinfection process for vehicles using chlorine dioxide and titanium dioxide with calculated re-treatment formulas and schedules based on bacterial infestation data. Systems and methods that include client devices and servers that monitor and control a chemical disinfection process. The system generates a surety arrangement that facilitates re-treatment and electronic notification alerts to chemical solution vendors, dealers and vehicle owners.

9 Claims, 19 Drawing Sheets

Related U.S. Application Data

(60) Provisional application No. 62/409,712, filed on Oct. 18, 2016.

(51) Int. Cl.
*A61L 101/34* (2006.01)
*A61L 101/02* (2006.01)

(52) U.S. Cl.
CPC ....... *A61L 2202/15* (2013.01); *A61L 2202/25* (2013.01); *G05B 2219/37399* (2013.01)

(58) Field of Classification Search
CPC ...... G05B 2219/37399; G05B 19/4155; A01N 31/08; A01N 59/16
See application file for complete search history.

(56) References Cited

U.S. PATENT DOCUMENTS

| | | | |
|---|---|---|---|
| 7,521,394 B2 | 4/2009 | Xie et al. | |
| 8,195,535 B2 | 6/2012 | Nagalla et al. | |
| 8,583,551 B2 | 11/2013 | Littrell et al. | |
| 8,709,341 B2 | 4/2014 | Day et al. | |
| 8,791,044 B2 | 7/2014 | Varma et al. | |
| 9,055,751 B2 | 6/2015 | Averett et al. | |
| 9,358,502 B2 | 6/2016 | Maltby et al. | |
| 9,392,795 B2 | 7/2016 | Averett et al. | |
| 9,724,440 B2 | 8/2017 | Bugenske et al. | |
| 9,925,529 B2 | 3/2018 | Balikhin et al. | |
| 10,434,203 B2 | 10/2019 | Averett et al. | |
| 2003/0220221 A1 | 11/2003 | Mcdonald et al. | |
| 2008/0040129 A1 | 2/2008 | Cauwels et al. | |
| 2008/0215505 A1 | 9/2008 | Reynolds | |
| 2008/0270193 A1 | 10/2008 | Beikmann | |
| 2008/0277466 A1 | 11/2008 | Dohm et al. | |
| 2008/0317959 A1 | 12/2008 | Baldi et al. | |
| 2009/0057401 A1 | 3/2009 | Brott et al. | |
| 2009/0286676 A1 | 11/2009 | Kim et al. | |
| 2010/0234263 A1 | 9/2010 | Wasan et al. | |
| 2010/0260644 A1* | 10/2010 | Day | A61L 9/00 29/527.4 |
| 2011/0143923 A1 | 6/2011 | Bette et al. | |
| 2011/0150753 A1 | 6/2011 | Kim et al. | |
| 2013/0118995 A1 | 5/2013 | Hawkins et al. | |
| 2013/0180931 A1 | 7/2013 | Owen | |
| 2014/0048494 A1 | 2/2014 | Simmons, Jr. | |
| 2014/0369953 A1* | 12/2014 | Purschwitz | A01N 35/02 514/718 |
| 2015/0039486 A1 | 2/2015 | Huynh et al. | |
| 2017/0032376 A1 | 2/2017 | Blackmon | |
| 2017/0202224 A1 | 7/2017 | Cozzi | |
| 2019/0001015 A1 | 1/2019 | Fiedler | |
| 2020/0315319 A1* | 10/2020 | Samain | B01F 33/8442 |

FOREIGN PATENT DOCUMENTS

| | | | |
|---|---|---|---|
| DE | 102012024739 A1 | 8/2013 | |
| JP | 10273649 A | 10/1998 | |
| JP | 2003306087 A | 10/2003 | |
| JP | 4523344 B2 | 8/2010 | |
| JP | 6017608 B2 | 11/2016 | |
| JP | 2019059642 A | 4/2019 | |
| KR | 200407716 Y1 | 2/2006 | |
| KR | 20120036734 A | 4/2012 | |
| KR | 20150001517 A | 1/2015 | |
| KR | 20170002909 A | 1/2017 | |
| WO | 9623051 A1 | 8/1996 | |
| WO | WO-0049119 A1 * | 8/2000 | A01N 59/16 |
| WO | 2005007483 | 1/2005 | |
| WO | WO-2007088151 A1 * | 8/2007 | B01J 35/004 |
| WO | WO-2009029854 A1 * | 3/2009 | B01D 53/8628 |
| WO | 2013045071 A2 | 8/2013 | |
| WO | 2016093770 | 8/2016 | |
| WO | 2017034487 | 4/2017 | |
| WO | 2017160114 | 9/2017 | |
| WO | 2018001175 A1 | 1/2018 | |
| WO | 2019074386 A1 | 4/2019 | |

OTHER PUBLICATIONS

"Our Car Wash Services," Waterway® Carwash, waterway.com, May 18, 2015. https://web.archive.org/web/20150518062414/http://www.waterway.com:80/carwash-services/.

"AutoBell® Unlimited Plan," AutoBell Car Wash, autobell.com, accessed: Oct. 2017. https://www.autobell.com/services-pricing/autobell-unlimited-plan.html.

Generating Color from Polydisperse, Near Micron-Sized TiO2 Particles, accessed: Oct. 16, 2017. http://pubs.acs.org/doi/abs/10.1021/acsami.7b05312?journalCode=aamick&.

Liao, et al., Visible-Light Active Titanium Dioxide Nanomaterials with Bactericidal Properties. Nanomaterials (Basel). Jan. 2020; 10(1): 124. doi: 10.3390/nano10010124.

Kuhn, et al. Disinfection of Surfaces by Photocatalytic Oxidation With Titanium Dioxide and UVA Light, Chemosphere. Oct. 2003;53(1):71-7. doi: 10.1016/S0045-6535(03)00362-X.

Porta, et al. Titanium oxide nanoparticle dispersions in a liquid monomer and solid polymer resins prepared by sputtering. New J. Chem., 2016, 40, 9337; DOI: 10.1039/c6nj01624c.

* cited by examiner

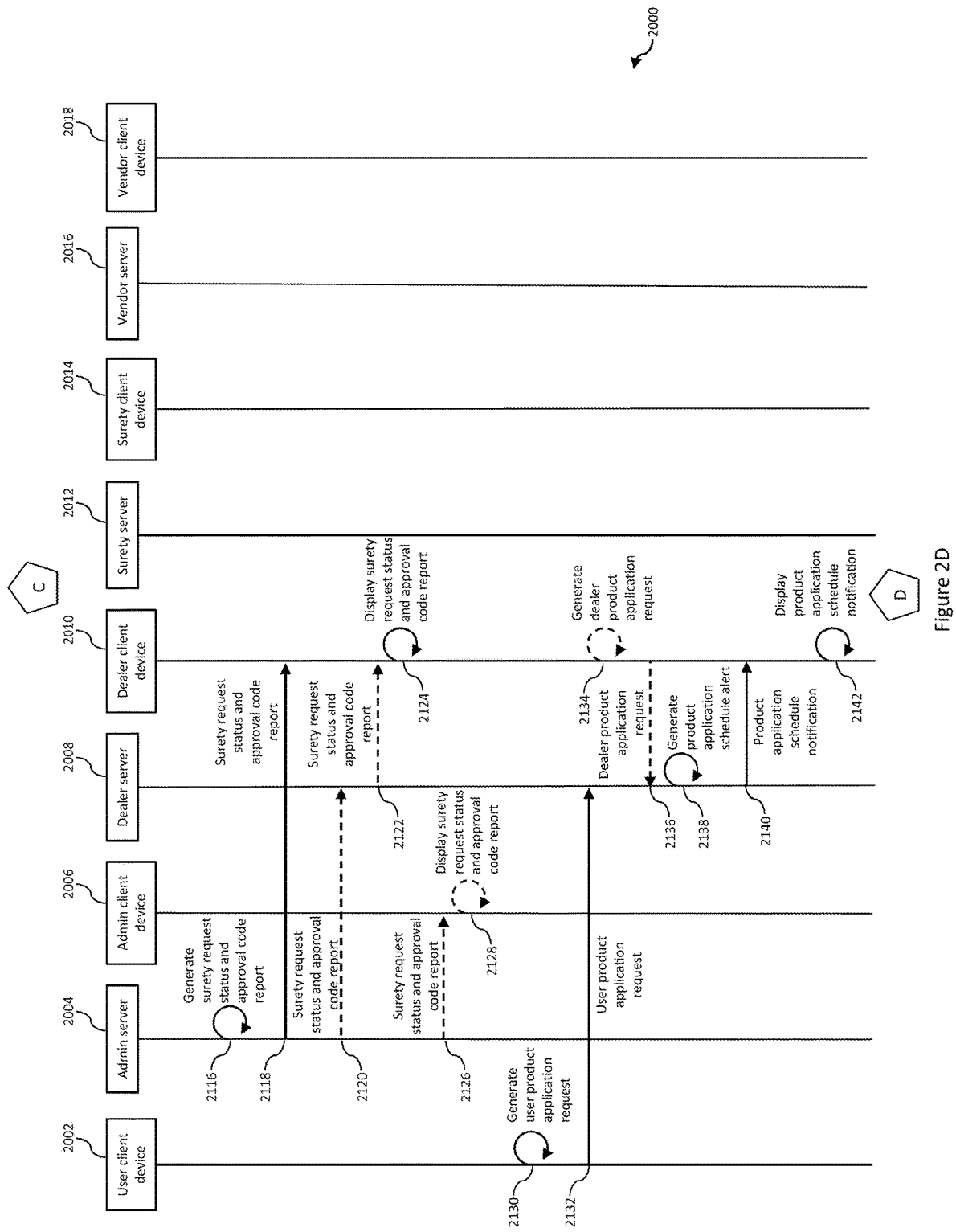

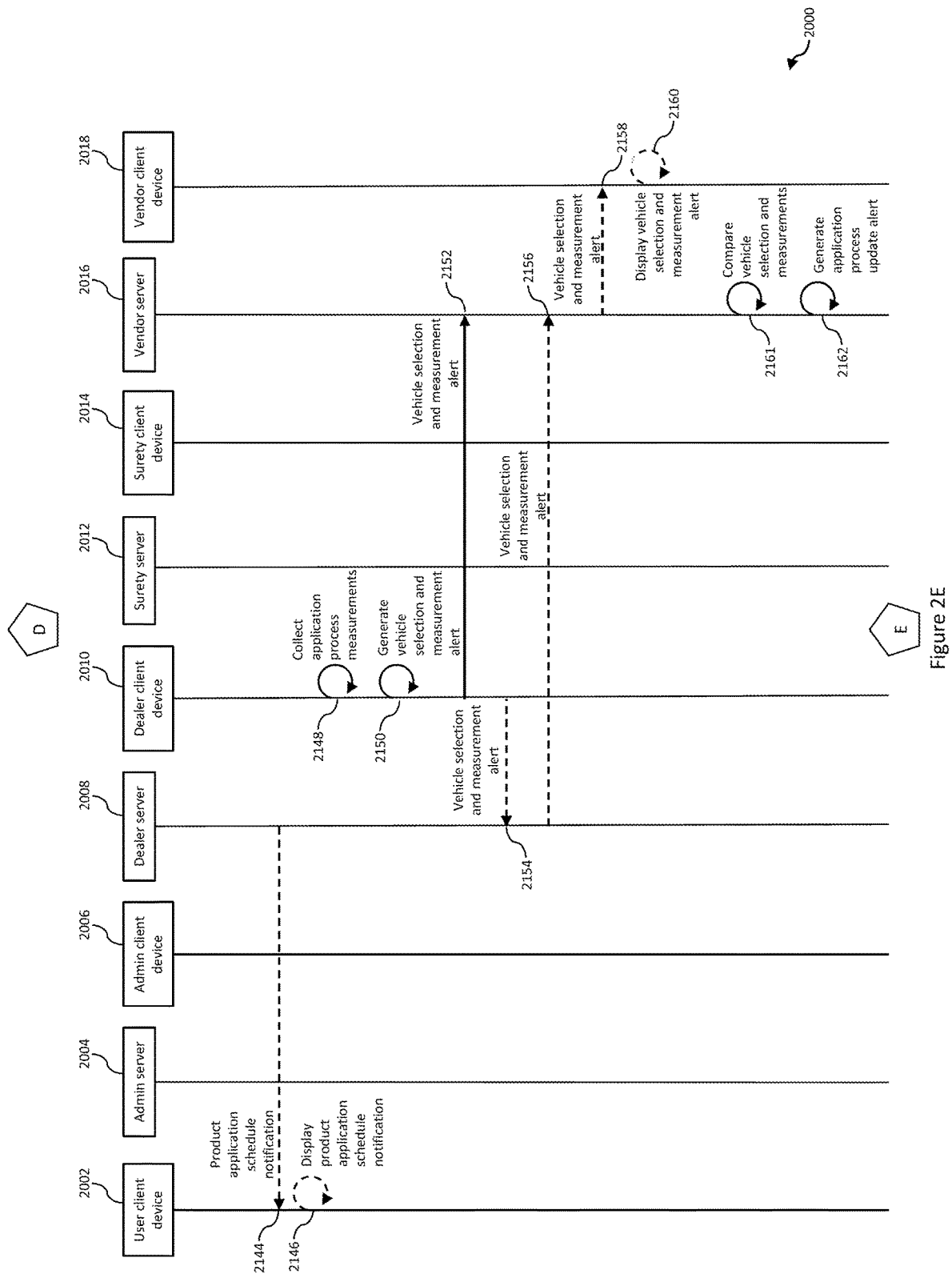

| Chemical Name | CAS # | Weight % |
|---|---|---|
| Alcohols, C12-C14, ethoxylated | 68439 – 50 - 9 | 0.1% - 10% |
| DI Water | 7732 – 18 – 5 | 70% - 80% |
| Titanium Dioxide | 13463 – 67 – 7 | 1% - 30% |
| Diethylamine Acetate | 20726 – 63 – 0 | 1% - 30% |
| Diethylammonium Dihydrogen Phosphate | 68109 – 72 – 8 | 1% - 30% |
| 2 – Propanol | 67 – 63 – 0 | 0.1% - 10% |
| Ethanol | 64 – 17 – 5 | 0.1% - 5% |
| Chlorine Dioxide | 10049 – 04 – 4 | 0.1% - 10% |
| Methyl Chloro Isothiazolinone | 26172 – 55 – 4 | 0.1% - 5% |
| Methyl Isothiazolinone | 2682 – 20 – 4 | 0.1% - 5% |

| Chemical Name | Weight % |
|---|---|
| Anatase Doped TiO2 | 1.50% - 15.00% |
| 2-amino-2-ethyl-1,3 propanediol | .10% - 1.00% |
| Thymol | .30% - 1.00 % |
| Fragrance | .001% - .30% |
| Deionized Water | 82.70% - 98.01% |

METHOD OF CHEMICALLY DISINFECTING A VEHICLE

CROSS-REFERENCE TO RELATED APPLICATIONS

This application is a continuation in part of U.S. application Ser. No. 15/787,650, filed Oct. 18, 2017, which claims priority to U.S. application Ser. No. 62/409,712, filed Oct. 18, 2016. Each patent application identified above is incorporated here by reference in its entirety to provide continuity of disclosure.

FIELD OF THE INVENTION

The present disclosure relates to systems and methods of vehicle disinfection including application and re-application of chemical suspensions in vaporized form. More particularly, the disclosure relates to systems in methods for assuring program re-application and maximization of disinfection efficacy.

BACKGROUND OF THE INVENTION

Titanium dioxide ("TiO2") compounds have a number of properties that make them particularly well-suited for application to high use surfaces, such as vehicle upholstery and interiors. In the presence of sunlight and water vapor, TiO2 forms hydroxyl radicals that are proven to reduce bacteria populations. TiO2 naturally absorbs light from the ultraviolet range of the electromagnetic spectrum, although different compounds can be formed to shift the absorbed range. For example, adding nitrogen may allow the compound to absorb light from the visible range. Once the energy from sunlight is absorbed, TiO2 compounds react with water vapor in the air to break one of the O—H bonds, transforming H2O into OH—, otherwise known as a hydroxyl radical. These OH— molecules effectively oxidize germs and bacteria through a reduction reaction. The reduction reaction disrupts the cell wall of the bacteria causing it to rupture.

Nevertheless, even in high concentrations, TiO2 is safe for human contact. Use of TiO2 has been approved by the FDA, and it is commonly used in many consumer items, such as sunscreen and sunblock.

TiO2 can be synthesized with a particle size of as low as one micron, making it capable of being embedded in many types of surfaces. TiO2's ability to embed itself in a wide variety of surfaces allows it to be effective in the highly varied interior of a vehicle. The interior of a vehicle often includes a wide variety of surfaces, such as cloth, leather, metal, plastic, polyester and glass. Moreover, vehicle interiors are prone to germ and bacteria build up over time. Further, vehicles are generally exposed to air and sunlight, making TiO2 a preferred solution for vehicle disinfection.

Regular cleaning of a surface that has been treated with TiO2 will eventually remove a majority of the TiO2 particles. Also, in time, TiO2 particles become embedded in surface dust. Thus, regardless of how the surface is treated, it will inevitably become necessary to re-treat the surface with TiO2 to maintain the benefits initially present.

The prior art has recognized TiO2 for vehicle applications, but has not solved the problems associated with efficient application of it for maximum disinfection.

For example, WO 2016/093770 to Lim discloses a system and method for cleaning a vehicle solution containing a nanoparticle metal oxide. However, the system is adapted to cleaning exterior surfaces of a vehicle, does not provide for re-application of the solution and fails to monitor the efficacy of the treatment.

U.S. Publication No. 2010/0234263 to Wasan, et al. discloses a solution comprised of water insoluble nanoparticles in a suspension, including titanium dioxide, for use in cleaning solutions including vehicle cleaning compounds. However, the solution does not leave deposits of TiO2 embedded in the vehicle surfaces, obviating the benefits of the photocatalytic reactions.

U.S. Publication No. 2009/0057401 to Brott, et al. discloses a method for providing periodic vehicle washes on a prepaid account by automatically identifying a vehicle with an affixed tag. However, the method does not include treatment of the vehicle interior with TiO2 nor does it vary the composition of the TiO2 solution based on test feedback.

WO 2017/034487 to Payakkawan discloses a system for dispersing TiO2 into the cabin of a vehicle and then exposing the TiO2 to an artificial source of UV light. However, the system does not use an aqueous solution of TiO2 that deposits nanoparticles in the surfaces for continuous self-cleaning over time, nor does it measure the efficacy of the treatment and prescribe appropriate re-treatment chemistry.

Thus, there is a need for systems and methods to properly create and disperse an aqueous solution of TiO2, to track and measure the efficacy of the TiO2 in preventing microbial build up, to alter re-treatment chemistry, and to generate and transmit electronic notifications to coordinate retreatment for maximum beneficial effect.

SUMMARY OF THE INVENTION

The present disclosure includes a preferred formation for a solution of TiO2 that can be dispersed into a vehicle's interior as an airborne suspension. Preferably, an airborne suspension of between 20 and 40 microns will leave the TiO2 embedded in most surfaces in a modern vehicle, allowing the photocatalytic reactions to take place. Other compounds are required, as will be further described. Certain compounds can be varied in amount based on test feedback, thereby altering the efficacy of the resulting suspension.

In a preferred embodiment, systems and methods for a chemical application process includes client devices and servers that monitor and control the chemical application process. The system generates an application process update alert based on a vehicle selection and collects measurement data from an application process based on the application process update alert. The system generates a surety request based on a user selection, the vehicle selection, and the measurement data. The system generates a status and approval code based on the surety request.

BRIEF DESCRIPTION OF THE DRAWINGS

In the detailed description of the preferred embodiments presented below, reference is made to the accompanying drawings.

FIG. 1 is a system diagram of a preferred embodiment.

FIGS. 2A-2H are a sequence diagram of a method performed by the system for performing chemical application process and monitoring re-treatment.

FIG. 3 is a method of reinsurance of treatment obligations between a dealership and an insurance underwriter.

FIG. 4 is a method for the performance of obligations between a dealership and a product vendor.

FIG. 5 is a method for the performance of obligations between a dealership and a vehicle owner.

FIG. 8 is a table of chemical components for a preferred embodiment of an aqueous solution of TiO2.

DETAILED DESCRIPTION OF THE INVENTION

Figure 1:
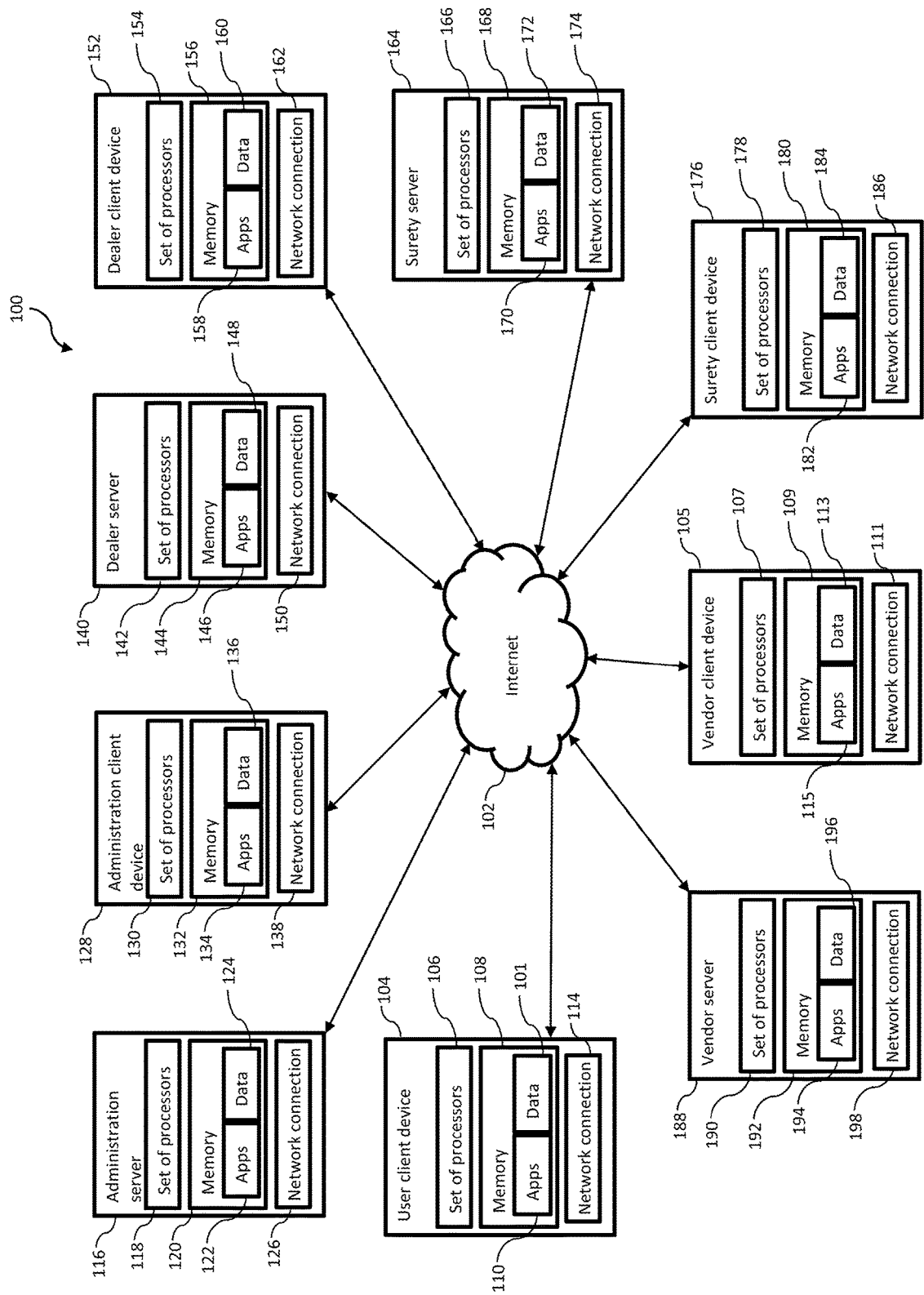
Figure 2A:
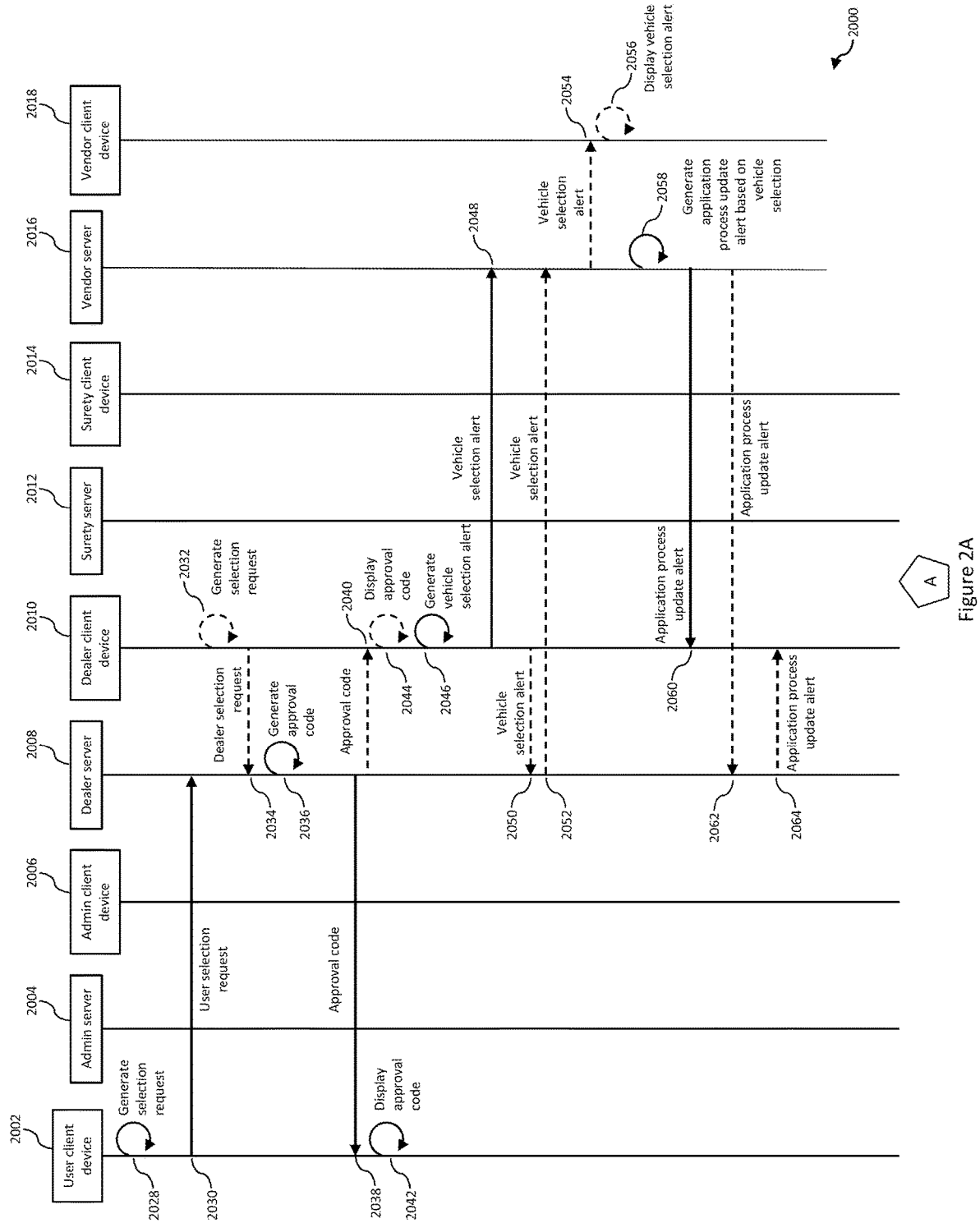
Figure 2B:
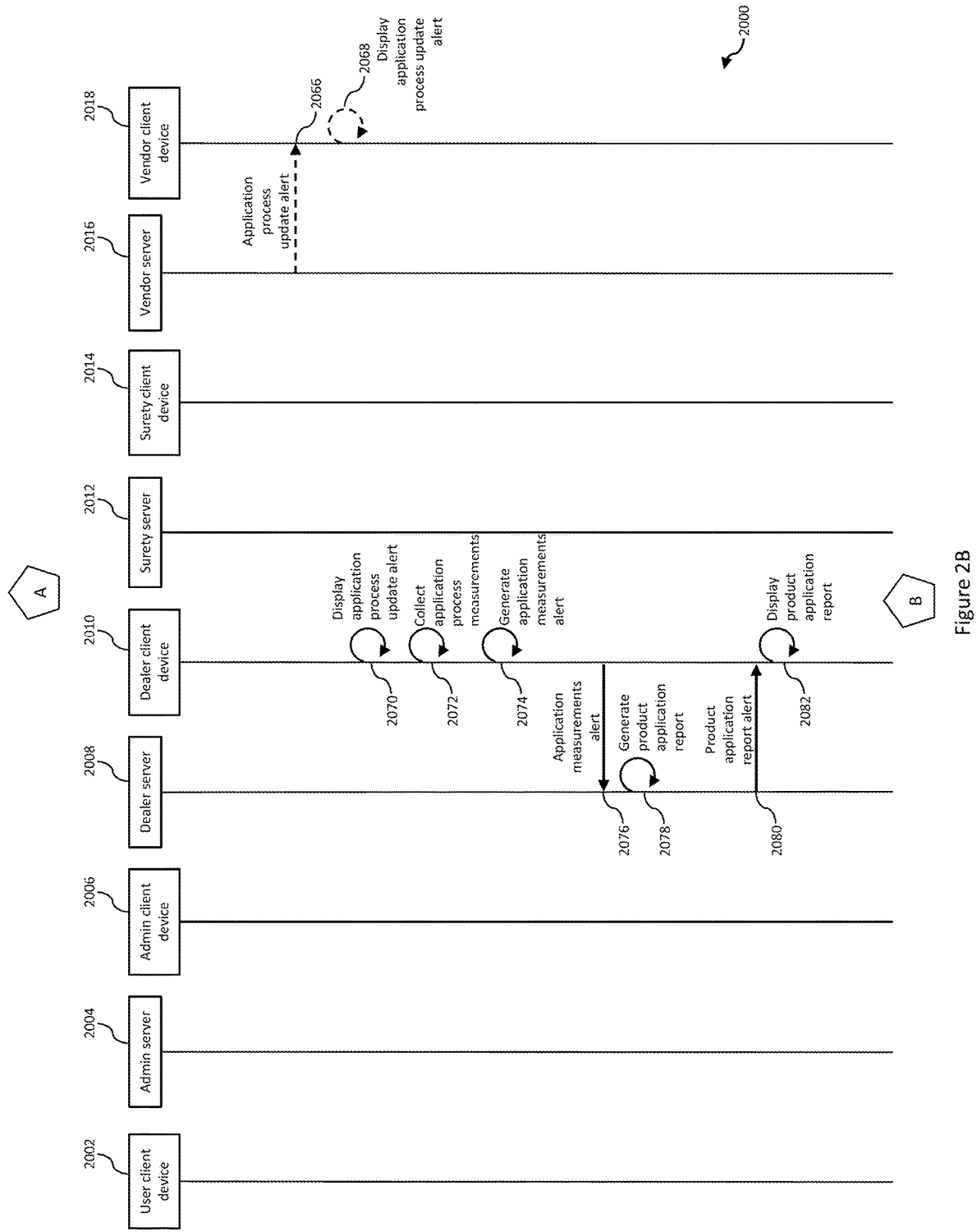
Figure 2C:
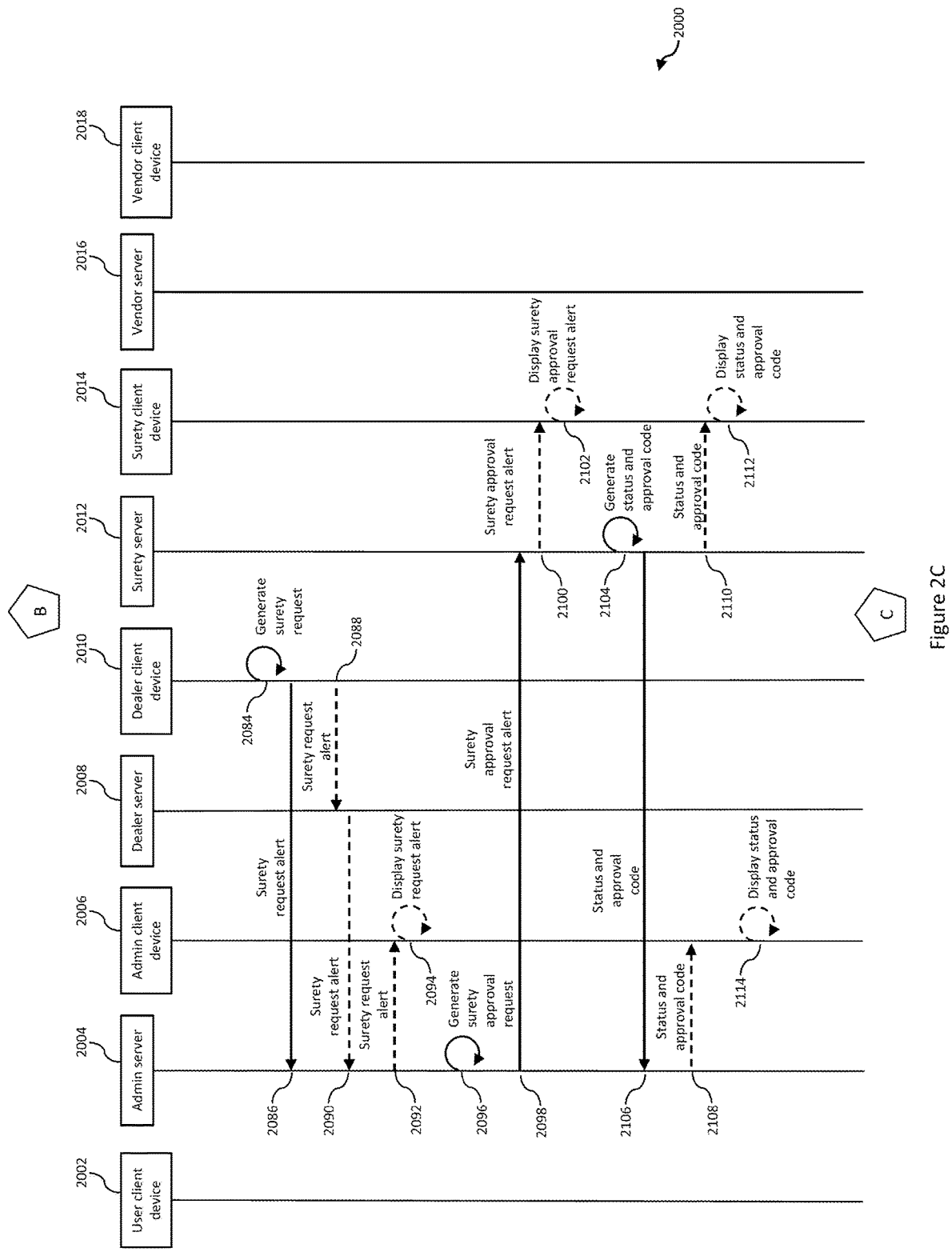
Figure 2F:
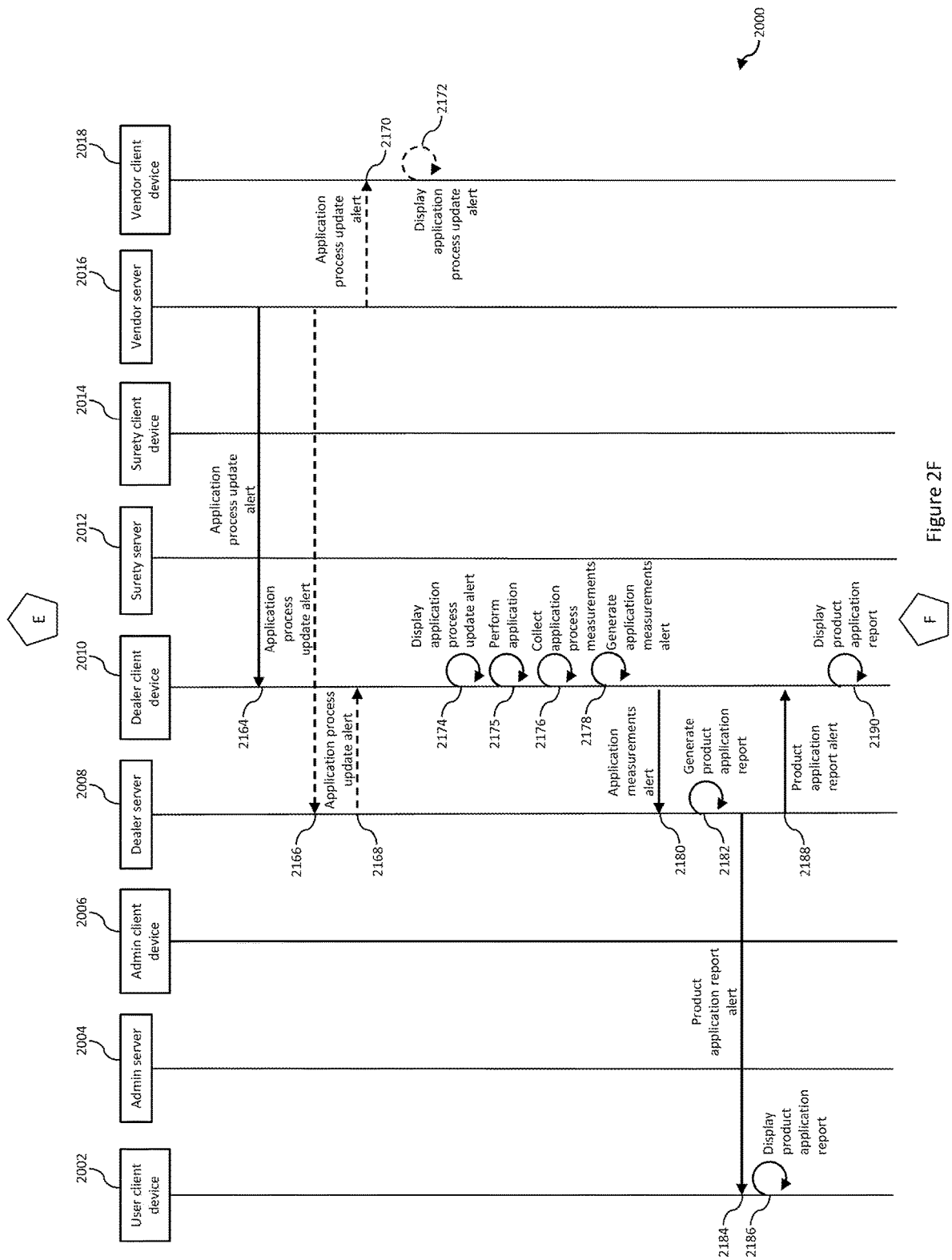
Figure 2G:
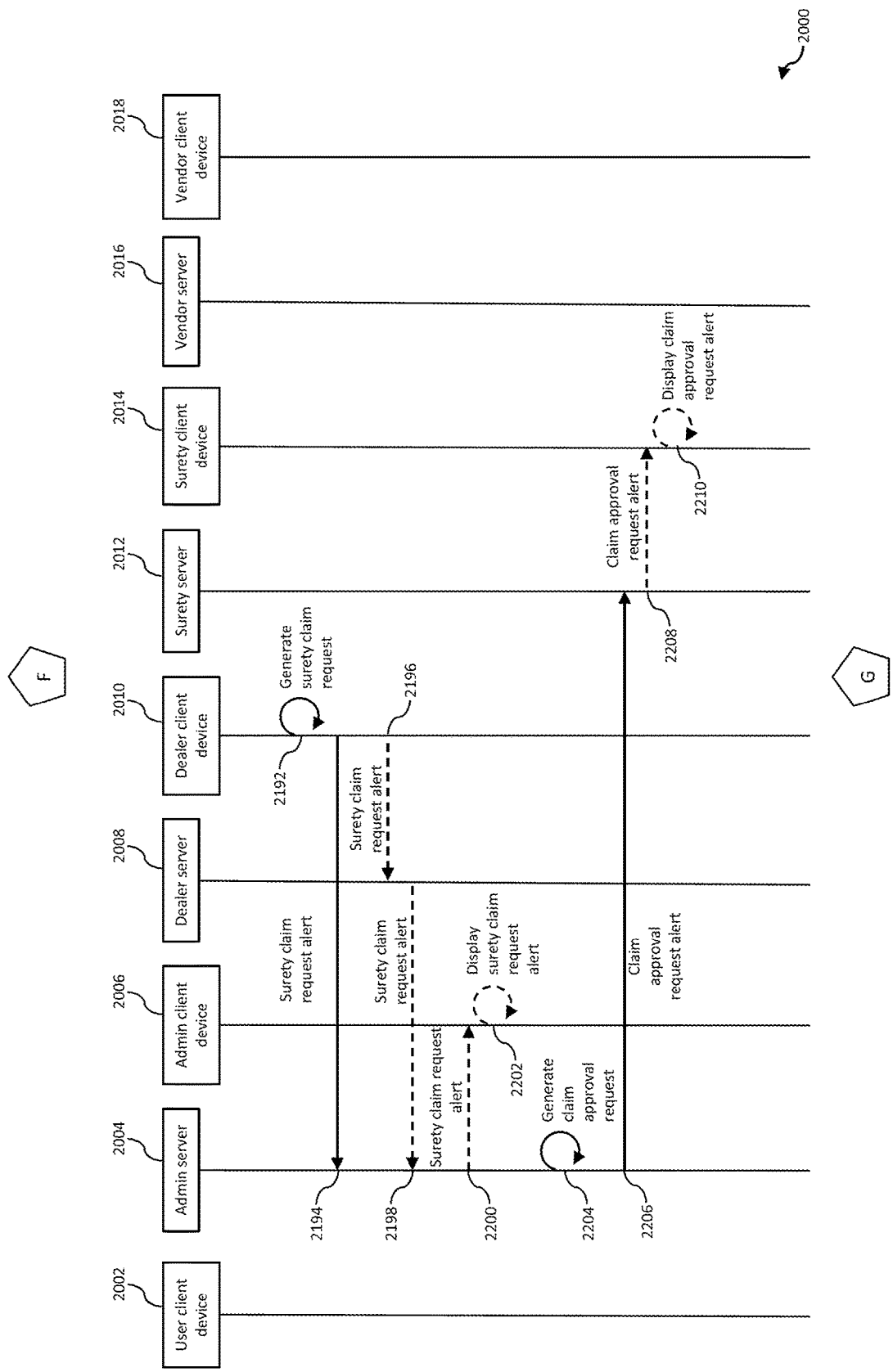
Figure 2H:
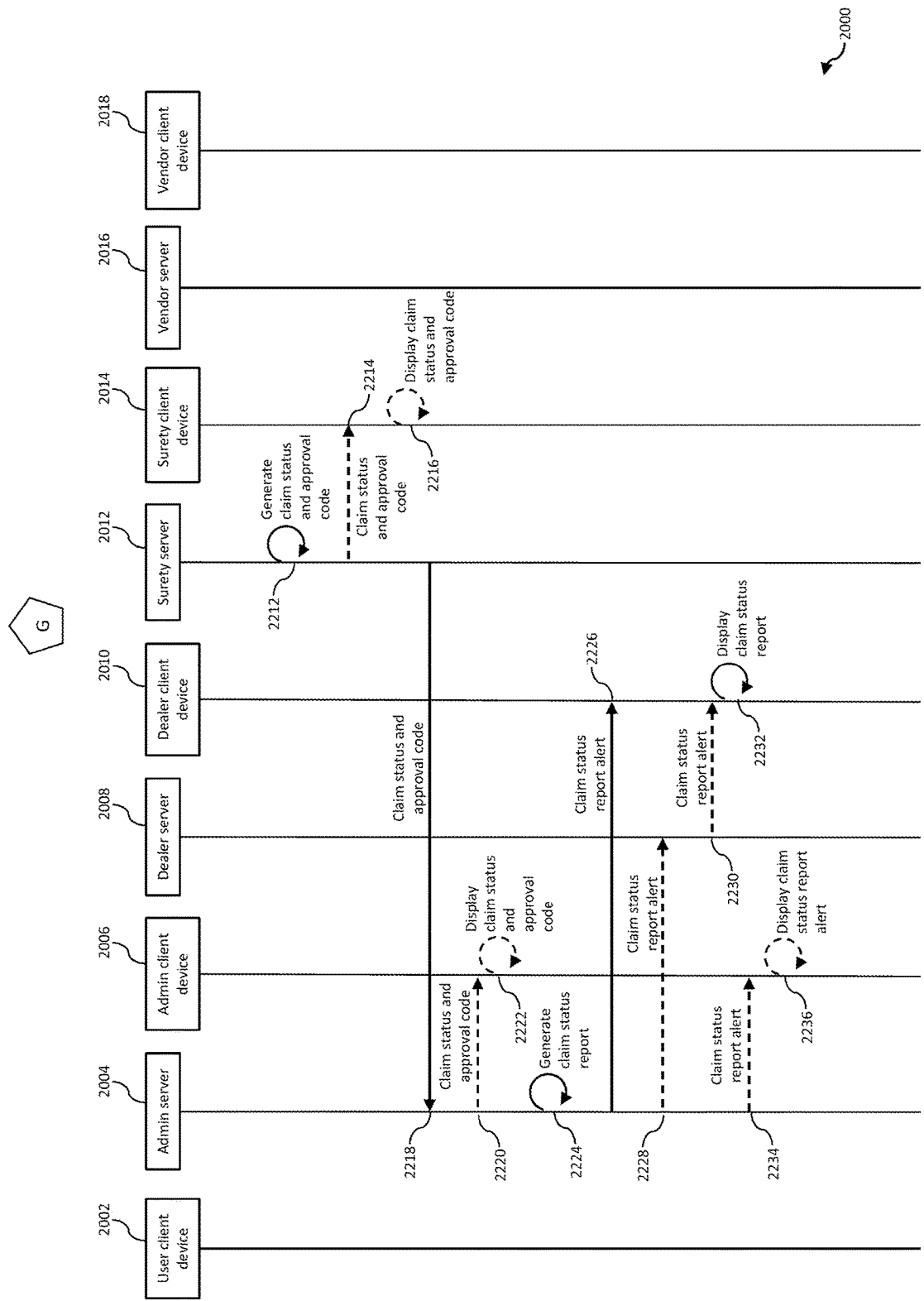

Referring to FIG. 1, system 100 includes several networked devices, including user client device 104, administration server 116, administration client device 128, dealer server 140, dealer client device 152, surety server 164, surety client device 176, vendor server 188, and vendor client device 105. System 100 operates to control the chemical application process based on measurements from the process and based on the type of vehicle to which the process is being applied.

User client device 104 includes: set of processors 106, memory 108, and network connection 114. Set of processors 106 includes at least one processor to execute programs stored in memory 108. Memory 108 includes apps 110 and data 101, which include instructions that are executable by set of processors 106 to perform the functions of system 100. Network connection 114 connects user client device 104 to internet 102. In a preferred embodiment, user client device 104 is used by the owner of the vehicle to purchase a package of at least one application spread out over at least one year and to schedule the applications.

Administration server 116 includes: set of processors 118, memory 120, and network connection 126. Set of processors 118 includes at least one processor to execute programs stored in memory 120. Memory 120 includes apps 122 and data 124, which include instructions that are executable by set of processors 118 to perform the functions of data 101. Network connection 126 connects administration server 116 to internet 102. In a preferred embodiment, administration server 116 is used to settle and control the transactions between the dealer and the surety through interactions with dealer server 140 and surety server 164.

Administration client device 128 includes: set of processors 130, memory 132, and network connection 138. Set of processors 130 includes at least one processor to execute programs stored in memory 132. Memory 132 includes apps 134 and data 136, which include instructions that are executable by set of processors 130 to perform the functions of data 124. Network connection 138 connects administration client device 128 to internet 102. In a preferred embodiment, administration client device 128 is used to control the processing performed by administration server 116.

Dealer server 140 includes: set of processors 142, memory 144, and network connection 150. Set of processors 142 includes at least one processor to execute programs stored in memory 144. Memory 144 includes apps 146 and data 148, which include instructions that are executable by set of processors 142 to perform the functions of data 136. Network connection 150 connects dealer server 140 to internet 102. In a preferred embodiment, dealer server 140 is used host a website that is accessible by user client device 104 and dealer client device 152 for purchasing, scheduling, and performing the chemical application process.

Dealer client device 152 includes: set of processors 154, memory 156, and network connection 162. Set of processors 154 includes at least one processor to execute programs stored in memory 156. Memory 156 includes apps 158 and data 160, which include instructions that are executable by set of processors 154 to perform the functions of data 148. Network connection 162 connects dealer client device 152 to internet 102. In a preferred embodiment, dealer client device 152 is used by a sales person at the dealership to initiate, setup the scheduling for, and perform the chemical application process as well as to interact with administration server 116 to submit new insurance requests and insurance claims.

Surety server 164 includes: set of processors 166, memory 168, and network connection 174. Set of processors 166 includes at least one processor to execute programs stored in memory 168. Memory 168 includes apps 170 and data 172, which include instructions that are executable by set of processors 166 to perform the functions of data 160. Network connection 174 connects surety server 164 to internet 102. In a preferred embodiment, surety server 164 is used to process insurance underwriting and claim requests.

Surety client device 176 includes: set of processors 178, memory 180, and network connection 186. Set of processors 178 includes at least one processor to execute programs stored in memory 180. Memory 180 includes apps 182 and data 184, which include instructions that are executable by set of processors 178 to perform the functions of data 172. Network connection 186 connects surety client device 176 to internet 102. In a preferred embodiment, surety client device 176 is used monitor and control the activity of surety server 164.

Vendor server 188 includes: set of processors 190, memory 192, and network connection 198. Set of processors 190 includes at least one processor to execute programs stored in memory 192. Memory 192 includes apps 194 and data 196, which include instructions that are executable by set of processors 190 to perform the functions of data 184. Network connection 198 connects vendor server 188 to internet 102. In a preferred embodiment, vendor server 188 is used to host a website that is accessed by dealer client device 152 to determine the appropriate settings for the chemical application process based on one or more of the type of vehicle, amount of interior space, amount of interior surface area, the number of previous applications, the length of time since the last application, and pre-application measurements.

Vendor client device 105 includes: set of processors 107, memory 109, and network connection 111. Set of processors 107 includes at least one processor to execute programs stored in memory 109. Memory 109 includes apps 115 and data 113, which include instructions that are executable by set of processors 107 to perform the functions of data 196. Network connection 111 connects vendor client device 105 to internet 102. In a preferred embodiment, vendor client device 105 controls and monitors the activity of vendor server 188 as well as updates the data, formulas, and information used to determine the parameters of the chemical application process.

Referring to FIGS. 2A through 2H, sequence diagram 2000 illustrates a preferred embodiment of the method used by system 100. The devices of system 100 generate alerts, requests, and messages that are sent to one or more other devices of system 100. Upon receiving alerts, requests, and messages, the respective devices activate and generate subsequent data alerts, requests, and messages based on one or more of: pre-existing data on the device; data received in the alerts, requests, and messages received by the device; and, data retrieved from other devices in response to the data received in the alerts, requests, and messages. In a preferred embodiment, for each of the messages generated and passed by the system, the device generating the message generates a cryptographic hash value from the information in the message, a random number, and a previously generated cryptographic hash value. In a preferred embodiment, the cryptographic hash value includes a predetermined number of leading zero bits in order to be acceptable by system 100. Several different random numbers are attempted in order to generate the cryptographic hash value with an acceptable number of leading zeros.

At step 2028, user client device 2002 generates a user selection request. In a preferred embodiment, user client device 2002 is activated in response to input from an input/output device such as a one or more of a keyboard, mouse, and touch sensitive screen and the input is used to identify the selection of the number of chemical process applications and the duration between the chemical process applications, which are encoded into the user selection request. In the context of TiO2 disinfection of a vehicle, the selection may be of a time period for re-application of the TiO2 solution, such as one re-application annually for 1, 5, 10, or 15 years.

At step 2030, user client device 2002 sends the user selection request to dealer server 2008.

At optional step 2032, dealer client device 2010 generates a dealer selection request. A dealer selection request is useful when the user has no smart phone and the dealer makes the selection for the user on the dealer client device.

At optional step 2034, dealer client device 2010 sends the dealer selection request, which is received by dealer server 2008.

At step 2036, an approval code is generated by dealer server 2008.

At step 2038, dealer server 2008 sends the approval code, which is received by user client device 2002.

At optional step 2040, dealer server 2008 sends the approval code, which is received by dealer client device 2010.

At step 2042, user client device 2002 displays the approval code.

At optional step 2044, dealer client device 2010 displays the approval code.

At step 2046, a vehicle selection alert is generated by dealer client device 2010.

At step 2048, the vehicle selection alert is sent from dealer client device 2010 to vendor server 2016.

At step 2050, the vehicle selection alert is sent from dealer client device 2010 to dealer server 2008.

At step 2052, the vehicle selection alert is sent from dealer server 2008 to vendor server 2016.

At step 2054, the vehicle selection alert is transmitted from vendor server 2016 and subsequently received by vendor client device 2018.

At optional step 2056, vendor client device 2018 displays the vehicle selection alert.

At step 2058, an application process update alert is generated by vendor server 2016.

At step 2060, vendor server 2016 sends the application process update alert, which is received by dealer client device 2010.

At optional step 2062, the application process update alert is sent from vendor server 2016 to dealer server 2008.

At optional step 2064, the application process update alert is sent from dealer server 2008 to dealer client device 2010.

At optional step 2066, the application process update alert is transmitted from vendor server 2016 and subsequently received by vendor client device 2018.

At optional step 2068, the application process update alert is displayed by vendor client device 2018.

At step 2070, dealer client device 2010 displays the application process update alert.

At step 2072, application process measurements are collected by dealer client device 2010. In a preferred embodiment, process measurements are the bacteria count from a selected surface sample or group of surface samples. In an alternate embodiment, the process measurements are TiO2 thickness for a given surface sample or group of surface samples.

At step 2074, dealer client device 2010 generates an application measurements alert. The application measurements alert, in a preferred embodiment, is a report including a summary of the application process measurements.

At step 2076, dealer client device 2010 sends the application measurements alert to dealer server 2008.

At step 2078, a product application report is generated by dealer server 2008.

At step 2080, dealer server 2008 sends the product application report to dealer client device 2010.

At step 2082, the product application report is displayed by dealer client device 2010.

At step 2084, a surety request is generated by dealer client device 2010. In a preferred embodiment, the surety request is a request from the dealer, to the administrator, for initiation of an insurance contract for the TiO2 re-application.

At step 2086, a surety request alert is sent from dealer client device 2010 to administration server 2004.

At optional step 2088, the surety request alert is sent from dealer client device 2010 to dealer server 2008.

At optional step 2090, dealer server 2008 sends the surety request alert to administration server 2004.

At optional step 2092, the surety request alert is sent from administration server 2004 to administration client device 2006.

At step 2094, the surety request alert is displayed by administration client device 2006.

At step 2096, a surety approval request is generated by administration server 2004. In a preferred embodiment, the administrator requests an insurance contract from the surety to insure the TiO2 re-application.

At step 2098, administration server 2004 sends a surety approval request alert to surety server 2012.

At optional step 2100, surety server 2012 sends the surety approval request alert to surety client device 2014.

At optional step 2102, surety client device 2014 displays the surety approval request alert.

At step 2104, a status and approval code is generated by surety server 2012. In a preferred embodiment, the approval code is generated when the surety issues an insurance contract for re-application of the TiO2.

At step 2106, the status and approval code is transmitted from surety server 2012 and subsequently received by administration server 2004.

At optional step 2108, administration server 2004 sends the status and approval code, which is received by administration client device 2006.

At optional step 2110, the status and approval code is sent from surety server 2012 to surety client device 2014.

At optional step 2112, surety client device 2014 displays the status and approval code.

At optional step 2114, administration client device 2006 displays the status and approval code.

At step 2116, a status and approval code report is generated by administration server 2004.

At step 2118, the status and approval code report is transmitted from administration server 2004 and subsequently received by dealer client device 2010.

At optional step 2120, the status and approval code report is sent from administration server 2004 to dealer server 2008.

At optional step 2122, the status and approval code report is transmitted from dealer server 2008 and subsequently received by dealer client device 2010.

At step 2124, dealer client device 2010 displays the status and approval code report.

At optional step 2126, administration server 2004 sends the status and approval code report to administration client device 2006.

At optional step 2128, administration client device 2006 displays the status and approval code report.

At step 2130, a user product application request is generated by user client device 2002.

At step 2132, user client device 2002 sends the user product application request, which is received by dealer server 2008.

At optional step 2134, a dealer product application request is generated by dealer client device 2010.

At optional step 2136, dealer client device 2010 sends the dealer product application request to dealer server 2008.

At step 2138, an application schedule is calculated and an alert is generated by dealer server 2008.

At step 2140, the product application schedule alert is sent from dealer server 2008 to dealer client device 2010.

At step 2142, the product application schedule alert is displayed by dealer client device 2010.

At optional step 2144, dealer server 2008 sends the product application schedule alert to user client device 2002.

At optional step 2146, the product application schedule alert is displayed by user client device 2002.

At step 2148, application process measurements are collected by dealer client device 2010. Hence, efficacy of the TiO2 re-application is measured through bacteria count or TiO2 thickness for a given surface or set of surfaces. This measurement is taken before the second application of TiO2 to the vehicle.

At step 2150, a vehicle selection and measurement alert is generated by dealer client device 2010. In a preferred embodiment, the vehicle selection is made by the dealer in order to identify which vehicle is being treated.

At step 2152, the vehicle selection and measurement alert is sent from dealer client device 2010 to vendor server 2016.

At optional step 2154, the vehicle selection and measurement alert is sent from dealer client device 2010 to dealer server 2008.

At optional step 2156, the vehicle selection and measurement alert is sent from dealer server 2008 to vendor server 2016.

At optional step 2158, vendor server 2016 sends the vehicle selection and measurement alert to vendor client device 2018.

At optional step 2160, vendor client device 2018 displays the vehicle selection and measurement alert.

At step 2161, the vehicle selection and the measurements are compared. In a preferred embodiment, the comparison is against one or more formulas in a database that identify the spray pressure, spray duration, and chemical composition as functions of the vehicle interior volume, vehicle interior surface area. The database also includes one or more tables that specify changes to spray pressure, spray duration, and chemical composition based on the materials of the interior and manufacturer of the vehicle. Spray pressure, spray duration, and chemical composition are all included in the settings and parameters in an application process update alert.

If the measurement is below about 50%, of its prior level, then substantially the same particle size, chlorine dioxide percentage, and pressure are used as from that last treatment. In a preferred embodiment, when the bacteria level, measured in relative light units (RLUs), is in a range of about 50% to about 70% of its prior level, then the particle size of the airborne suspension is adjusted from about 30 microns downward to about 20 microns. In this way, a greater depth of surface penetration is achieved. When the bacteria level is in the range of about 70% to about 90% of the prior level then in addition to reduction in particle size, the percentage of chlorine dioxide by weight is increased by about 5%. In this way, the suspension is adjusted to become more lethal to recurring bacteria. In situations above about 90%, the application pressure and flowrate are increased by about 20% in addition to the adjustment in particle size and increased chlorine dioxide. In a preferred embodiment, initial application pressure is between about 90 psi and about 100 psi. In a preferred embodiment, initial application flowrate is 2.5 oz/min.

At step 2162, vendor server 2016 generates an application process update alert. In a preferred embodiment, an application process update alert is generated when an application of the TiO2 suspension is complete.

At step 2164, vendor server 2016 sends the application process update alert, which is received by dealer client device 2010.

At optional step 2166, vendor server 2016 sends the application process update alert to dealer server 2008.

At optional step 2168, the application process update alert is sent from dealer server 2008 to dealer client device 2010.

At optional step 2170, vendor server 2016 sends the application process update alert to vendor client device 2018.

At optional step 2172, vendor client device 2018 displays the application process update alert.

At step 2174, the application process update alert is displayed by dealer client device 2010.

Figure 5:
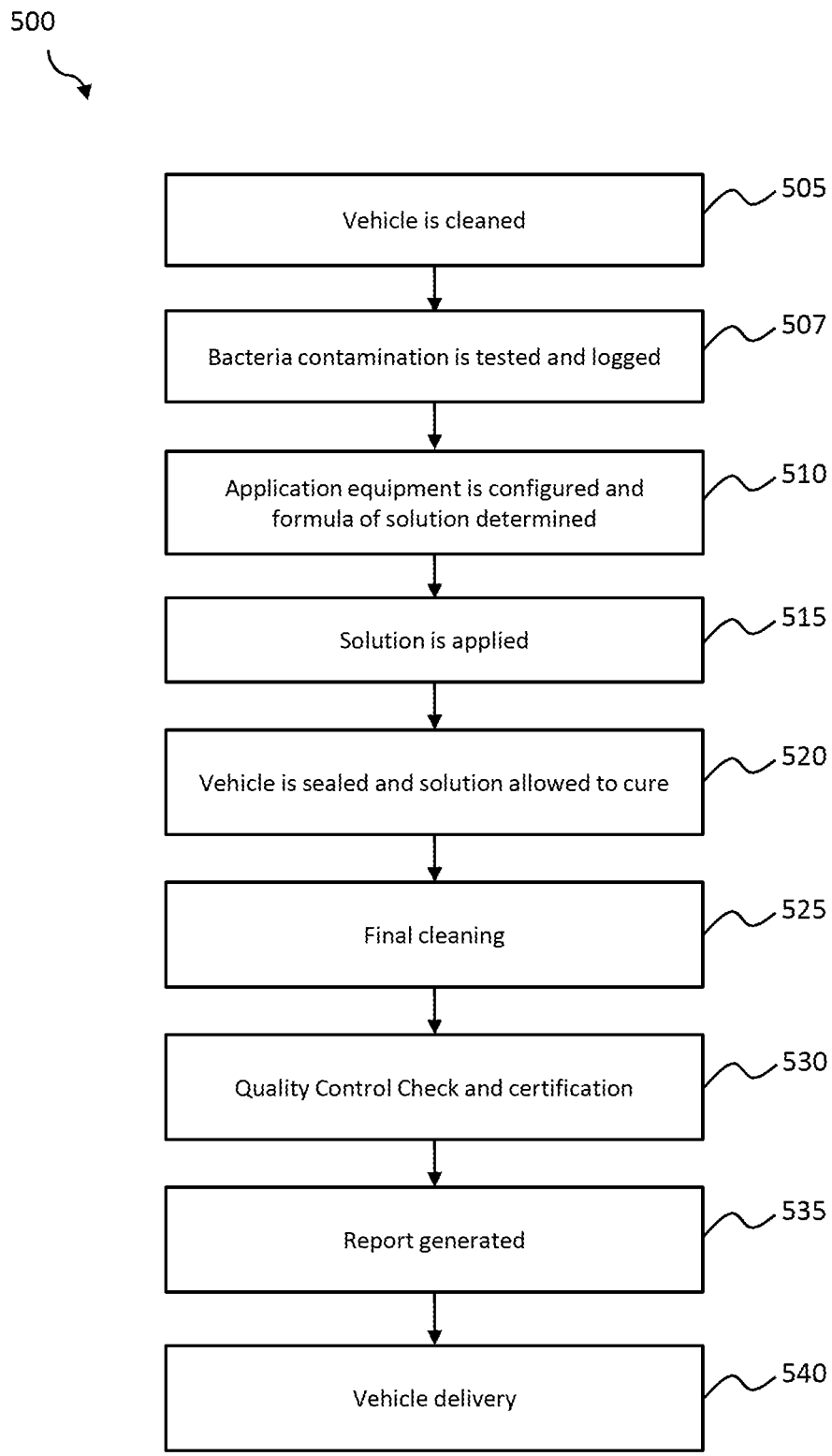
Figure 6:
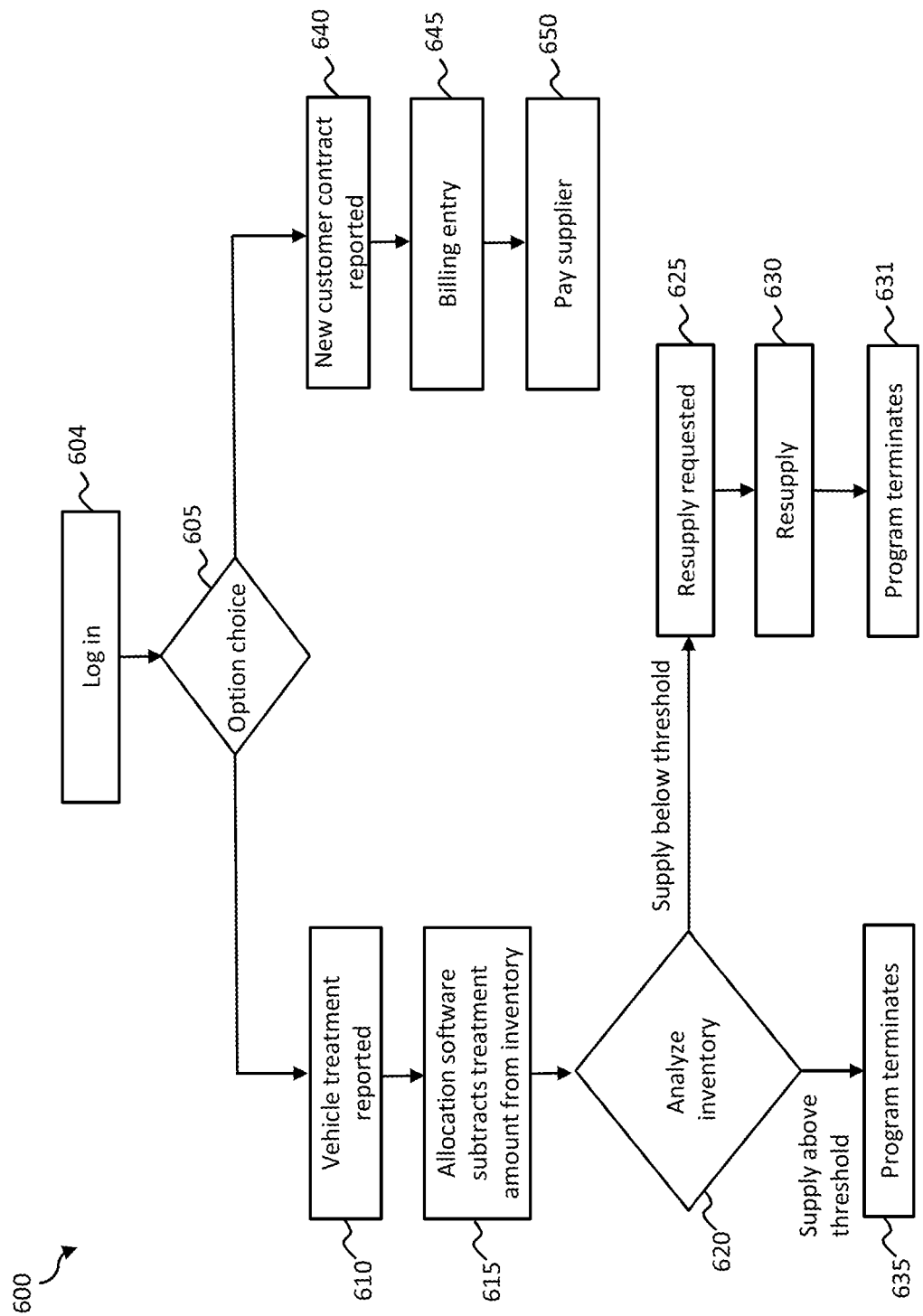
FIG. 6 is a method for the performance of obligations between dealership and product vendor.
Figure 7:
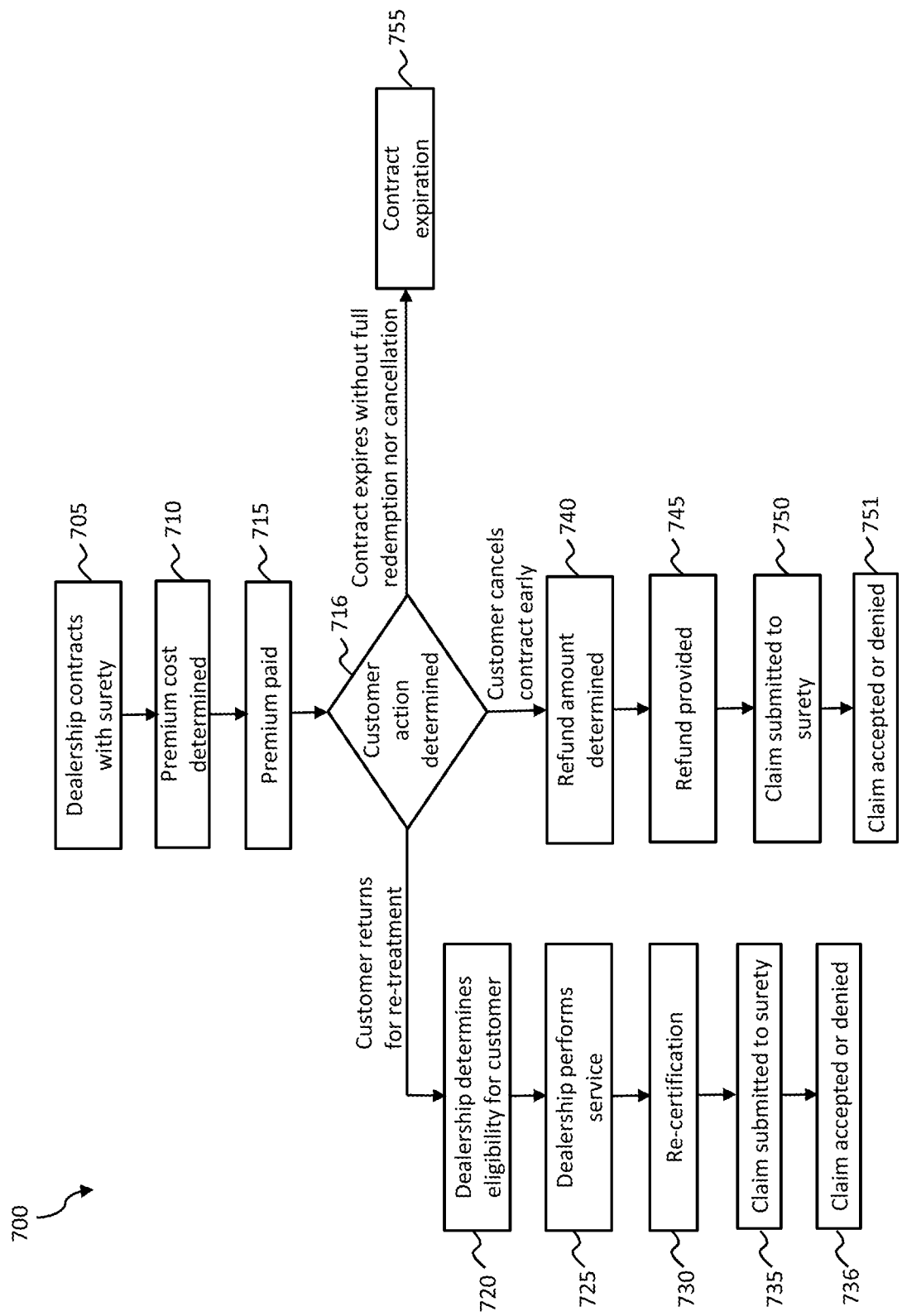
FIG. 7 is a method for the performance of obligations between dealership and Insurance Underwriter.

At step 2175, the application process is performed, which is further described in FIG. 5. In a preferred embodiment, the user of dealer client device 2010 follows the instructions received from vendor server 2016 for generating correct chemical composition of the TiO2 solution and using the correct pressure spray settings.

At step 2176, dealer client device 2010 collects application process measurements. In a preferred embodiment, this measurement is taken after the second application of TiO2 so that a comparison can be made prior application process measurements.

At step 2178, an application measurements alert is generated by dealer client device 2010.

At step 2180, the application measurements alert is sent from dealer client device 2010 to dealer server 2008.

At step 2182, a product application report is generated by dealer server 2008. In a preferred embodiment, the report includes a measure of efficacy of the TiO2 application and the number of TiO2 applications left for the term of the insurance contract.

At step 2184, the product application report is sent from dealer server 2008 to user client device 2002.

At step 2186, user client device 2002 displays the product application report.

At step 2188, the product application report is transmitted from dealer server 2008 and subsequently received by dealer client device 2010.

At step 2190, dealer client device 2010 displays the product application report.

At step 2192, a surety claim request is generated by dealer server 2008. In a preferred embodiment, the claim request is a request for payment under the insurance contract.

At step 2194, dealer client device 2010 sends a surety claim request alert to administration server 2004.

At optional step 2196, dealer client device 2010 sends the surety claim request alert, which is received by dealer server 2008.

At optional step 2198, the surety claim request alert is transmitted from dealer server 2008 and subsequently received by administration server 2004.

At optional step 2200, the surety claim request alert is sent from administration server 2004 to administration client device 2006.

At optional step 2202, administration client device 2006 displays the surety claim request alert.

At step 2204, a claim approval request is generated by administration server 2004.

At step 2206, a claim approval request alert is transmitted from administration server 2004 and subsequently received by surety server 2012.

At optional step 2208, the claim approval request alert is sent from surety server 2012 to surety client device 2014.

At optional step 2210, surety client device 2014 displays the claim approval request alert.

At step 2212, surety server 2012 generates a claim status and approval code.

At optional step 2214, surety server 2012 sends the claim status and approval code, which is received by surety client device 2014.

At optional step 2216, surety client device 2014 displays the claim status and approval code.

At step 2218, the claim status and approval code is transmitted from surety server 2012 and subsequently received by administration server 2004.

At optional step 2220, the claim status and approval code is transmitted from administration server 2004 and subsequently received by administration client device 2006.

At optional step 2222, the claim status and approval code is displayed by administration client device 2006.

At step 2224, a claim status report is generated by administration server 2004.

At step 2226, the claim status report is sent from administration server 2004 to dealer client device 2010.

At optional step 2228, administration server 2004 sends the claim status report to dealer server 2008.

At optional step 2230, the claim status report is transmitted from dealer server 2008 and subsequently received by dealer client device 2010.

At step 2232, the claim status report is displayed by dealer client device 2010.

At optional step 2234, administration server 2004 sends the claim status report to administration client device 2006.

At step 2236, administration client device 2006 displays the claim status report.

Figure 3:
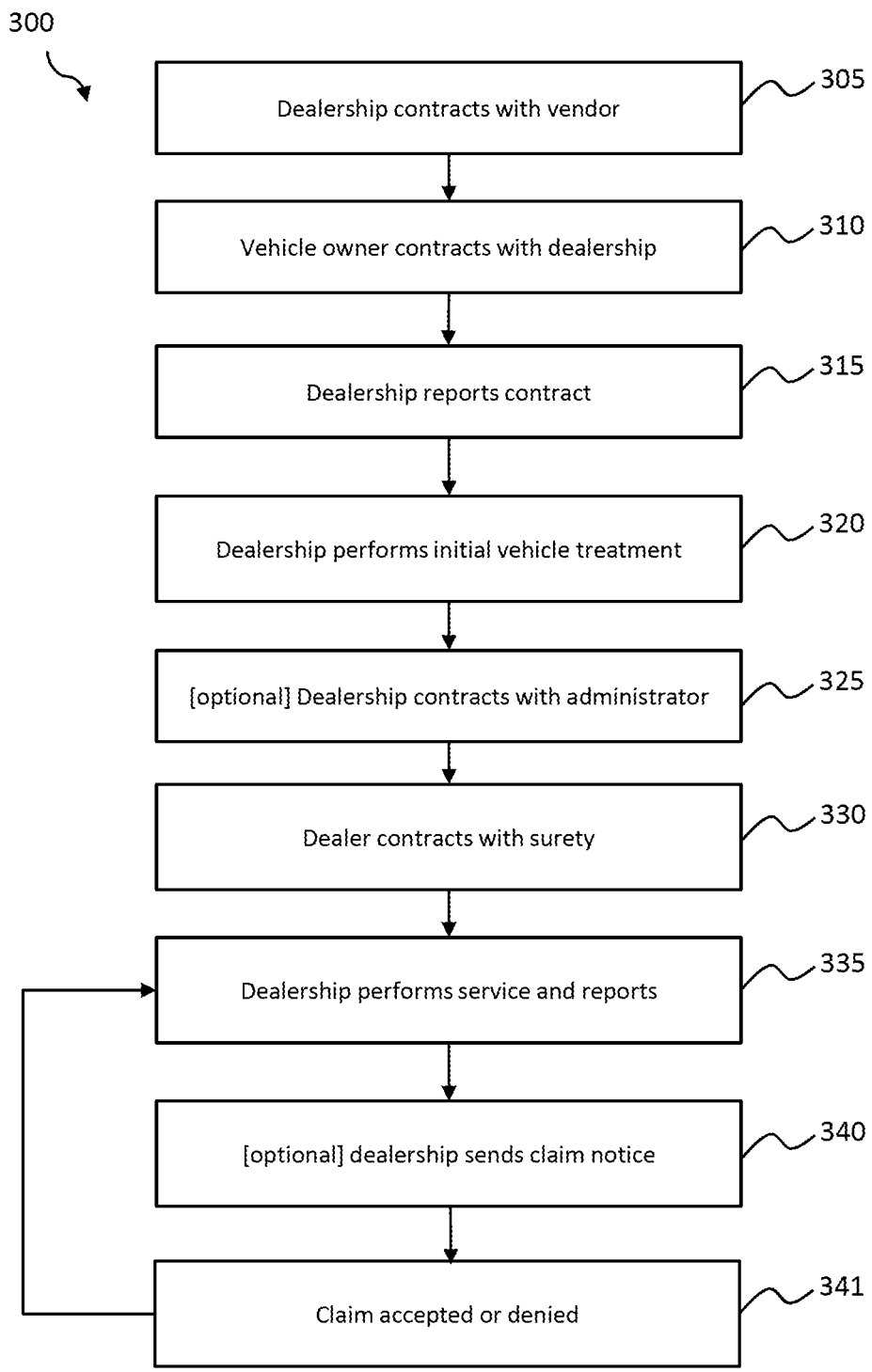

Referring to FIG. 3, a method 300 of organizing repeated treatments of TiO2 solution to a vehicle interior will be described. Beginning at step 305, the dealership enters into a contract with the product vendor, whereby the dealership agrees to use system 100. At step 310, a vehicle owner enters into a contract with the dealership, whereby the vehicle owner will receive treatments with the TiO2 solution. At step 315, the dealership reports that a contract has been agreed to via dealer client device 152, and the system 100 alerts the vendor. At step 320, the dealership treats the vehicle with TiO2 solution. At step 325, the dealership optionally enters into a contract with an administrator, whereby the administrator interfaces with surety servers 164 and surety client devices 176 on behalf of the dealership. At step 330, the dealership enters into a surety contract with a surety, whereby the surety guarantees the contract between the dealership and a vehicle owner. At step 335, the dealership performs additional treatments of the vehicle reports them via dealer client device 152. At step 340, the dealership may optionally generate and transmit a notice to the surety of a claim under the surety contract. At step 341, the claim is either accepted or denied. The method then repeats steps 335 through 341 as the vehicle owner returns to the dealership for future reapplications of the TiO2 solution, until the contract between the dealership and the vehicle owner expires.

Figure 4:
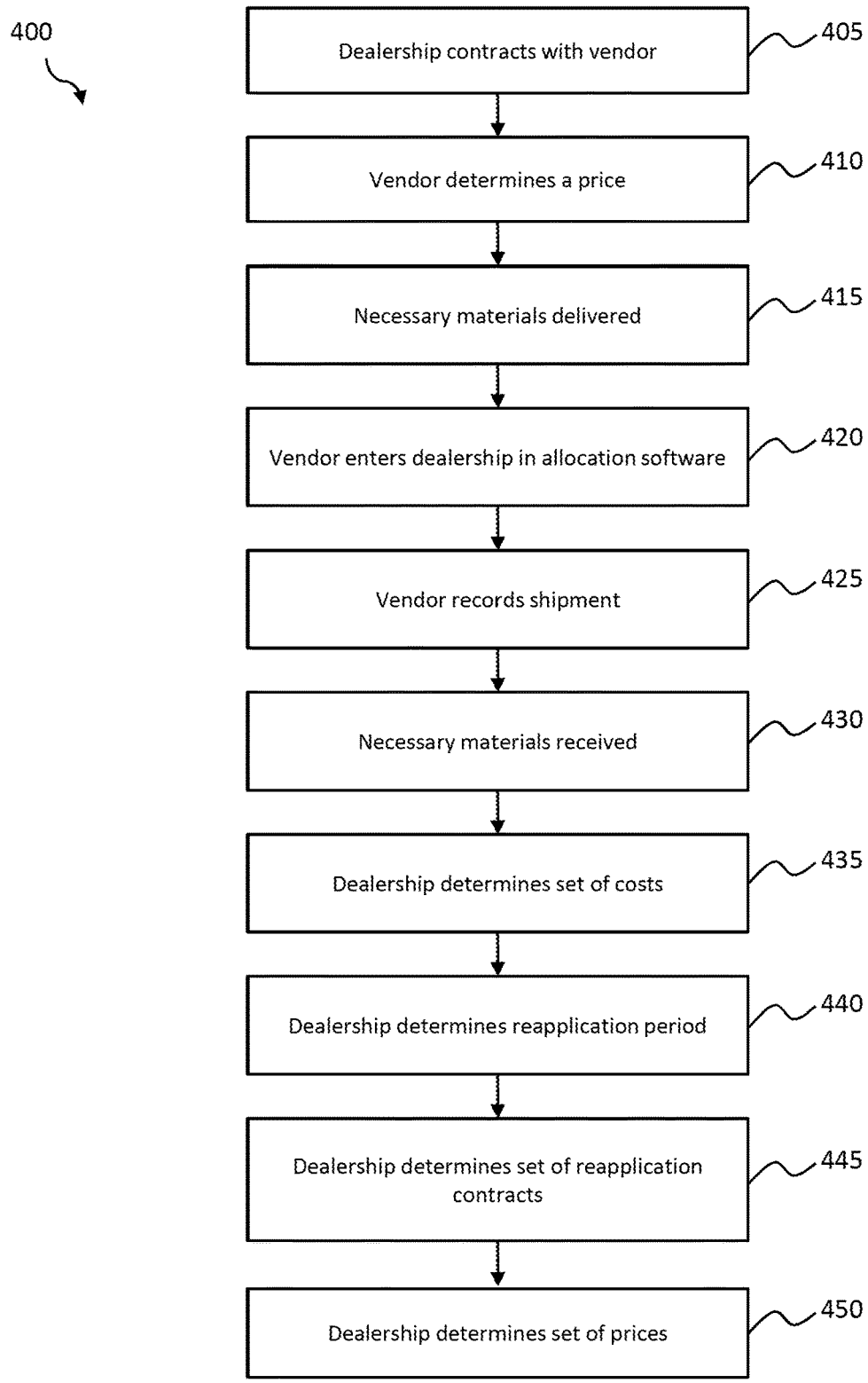

Referring to FIG. 4, a method 400 for generating and transmitting notices between a dealership and a vendor. Beginning at step 405, the dealership enters into a contract with the vendor. At step 410, the vendor determines a dealer cost Y. In one embodiment, Y is a fixed amount charged to the dealership, calculated based on the amount of TiO2 solution that the dealership orders. In another embodiment, Y is a recurring cost assessed to the dealership at set time intervals, such as monthly or quarterly. In a preferred embodiment, Y is a fixed cost per customer contract. At step 415, the vendor ships the dealership an initial amount B (in gallons) of TiO2 solution, equipment for the application of the TiO2 solution, and training materials instructing the dealership in the proper use of the equipment and application of the TiO2 solution. At step 420, the vendor enters dealership into the allocation software. The allocation software functions to track usage of TiO2 solution and generate corresponding shipment alerts and billing entries. In one embodiment, the allocation software runs on dealer server 140, and is configured to transmit notifications to vendor client device 105, vendor server 188, or both. In a preferred embodiment, the allocation software runs on the vendor server 188 and is accessible by vendor client device 105 and dealer client device 152 via the internet 102. At step 425, the vendor records in the allocation software the shipment of the TiO2 solution to the dealership. At step 430, the dealership receives the shipment of TiO2 solution, application equipment, and training materials, and trains the appropriate staff to treat vehicles with TiO2 solution. At step 435, the dealership determines a treatment price A. In one embodiment, A is a fixed cost per treatment. In another embodiment, A is a sliding scale depending on the number of previous treatments applied to that vehicle, with higher values of A assigned when the vehicle has gone for long periods of time without treatment. Other embodiments are possible, and determination of A may be influenced by a number of factors, including the make, model, and age of the vehicle, the climate, especially the amount of sunlight and moisture experienced or expected, and known driving habits of the vehicle owner, such as infrequent uses of the vehicle and storage away from sunlight. At step 440, the dealership determines a reapplication period P, measured in months. At the end of reapplication period P, the vehicle will need to be re-treated with TiO2 solution. In a preferred embodiment, reapplication period P is between about 6 and about 18 months, and ideally 12 months. At step 445, the dealership determines a set of treatment contracts [$K_1$, $K_2$, $K_3$ . . . ] to be offered to vehicle owners. Set of contracts [$K_1$, $K_2$, $K_3$ . . . ] may be offered in increments of reapplication period P. Vehicle owners may agree to enter into a contract $K_n$ such that $K_n$ lasts for (n×P) months and involves (n+1) treatments. At step 450, the dealership determines a set of prices [$X_1$, $X_2$, $X_3$ . . . ] corresponding to set of contracts [$K_1$, $K_2$, $K_3$ . . . ]. In a preferred embodiment:

$$X \geq (A(n+1)) + Y \qquad \text{Eq. 1}$$

where:
X=contract price
A=cost/application
n=number of treatments
Y=dealer cost

Referring to FIG. 5, a method 500 for the treatment of a vehicle with TiO2 solution. Beginning at step 505, the dealership cleans the interior of the vehicle in preparation for treatment of the interior with the TiO2 solution. Soap and water plus a diluted solution of chlorine bleach is recommended. The TiO2 solution is an aqueous solution of TiO2 that leaves TiO2 nanoparticles embedded in the surfaces of a vehicle's interior. Thorough cleaning is required before treatment with TiO2 solution to allow the TiO2 sufficient contact of the suspension with all interior surfaces. At step 507, bacteria contamination levels are tested and logged. At step 510, the dealership determines the formula of the TiO2 solution to be applied and configures the application equipment. In a preferred embodiment, the contamination test results are entered into the system, which then derives a proper formulation and pressure settings. In another embodiment, the dealer client device 152 receives notifications from vendor server 188 with instructions regarding the proper formula to use based on test results. In an alternate embodiment, the vendor prepares the solution and the dealership receives it pre-mixed based on a generalized application schedule. The application equipment is configured to produce the proper airborne suspension. In a preferred embodiment, the initial application includes particle sizes of between about 20 and 40 microns. In a preferred embodiment, the application equipment is a physical suspension vaporizer that is configured to produce droplets with a diameter of approximately 25 to 30 microns delivered at about 95 psi. In a preferred embodiment, the physical suspension vaporizer is a B&G fogger model no. 2300 available from B&G Equipment, Co. of Atlanta, Ga. In another preferred embodiment, the application equipment can be spray bottles, aerosol cans, or spray cans that produce droplets with a diameter of less than 100 microns. At step 515, the dealership seals all vehicle openings, then applies the suspension through an intake air vent or window of the vehicle. In one embodiment, approximately 4 ounces of TiO2 solution dispensed for a 4 passenger vehicle. In a preferred embodiment, the amount is calibrated based on the interior surface area known to exist for the make and model of the vehicle. The amount of adjustment is approximately about 20% less for 2 passenger vehicles and about 20% more for 6 passenger vehicles. In general, addition of about 20% more solution is added for every addition of 2 passenger capacity. At step 520, the vehicle resealed. The vehicle is left undisturbed for 1-2 minutes to allow the suspension to cure. In one preferred embodiment curing can be accelerated by application of ultraviolet light, preferably in the range of about 320 nm to about 395 nm. At step 525, interior surfaces are wiped, removing the excess (now dry) solution, leaving TiO2 nanoparticles embedded in all interior surfaces. At step 530, the vehicle is certified as treated. In one embodiment, the certification may comprise applying a sticker to the vehicle, indicating that it has been treated with the TiO2 solution. In another embodiment, the certification may comprise a database entry, recording that the vehicle has been treated with the TiO2 solution in the records of the dealership. In a preferred embodiment, the certification comprises placing a sticker with the date of the treatment on the vehicle windshield, to be replaced when future treatments are applied. At step 535, the dealership logs into the allocation software via dealer client device 152 and reports that a treatment was applied. At step 540, the dealership returns the vehicle to the owner.

Referring to FIG. 6, a method 600 for tracking the performance of the dealership and the vendor. Beginning at step 604, the dealership logs into the allocation software. At step 605, the dealership elects to either proceed to step 610 and report the treatment of a vehicle, or proceed to step 640 and report the existence of a new contract with a vehicle owner. Proceeding then to step 610, the dealership reports that a vehicle was treated with the TiO2 solution. The method continues to step 615, whereby the allocation software logs the treatment by the dealership, and updates a corresponding database entry to reflect a lower amount for the dealership's inventory amount of the TiO2 solution. In one embodiment, the allocation software subtracts amount of solution used from the inventory amount. At step 620, the allocation software compares the new database entry reflecting the dealership's inventory amount of solution to a threshold shipment amount. If the dealership has more inventory than the threshold shipment amount, then the method proceeds to step 635, and the program terminates. At step 620, if the dealership's inventory amount is less than the threshold amount, then the method proceeds to step 625. At step 625, the allocation software triggers a request for shipment from the vendor. At step 630, the vendor ships replacement supplies to the dealership. At step 631, the program terminates.

Returning to step 605, if the dealership reports a new contract, then the method proceeds to step 640. At step 640, the dealership uses the allocation software to record that a new contract for TiO2 solution treatments. The dealership inputs the relevant data for the contract, including the vehicle owner contact information, number of future retreatments of the vehicle and the time intervals at which retreatments are required. The method then proceeds to step 645, where the allocation software creates a billing entry, reflecting the amount Y owed by the dealership to the vendor. In one embodiment, the allocation software accumulates billing entries and generates a periodic bill sent to the dealership. The method then proceeds to step 650, whereby the dealership pays the vendor payment Y.

Referring to FIG. 7, a method 700 for generating and transmitting notices between a dealership and a surety. Beginning at step 705, the dealership enters into a surety contract with a surety, guaranteeing performance of the dealership's contract with a vehicle owner. At step 710, the surety determines a premium amount W. At step 715, the dealership pays W to the surety. At step 716, the dealership determines the customer action, and the method then proceeds in one of three ways. If the vehicle owner returns to the dealership for a retreatment of the TiO2 solution, then the method proceeds to step 720. If the vehicle owner cancels the contract with the dealership, then the method proceeds to step 740. If the contract between the dealership and the vehicle owner expires, then the method proceeds to step 755.

At step 720, the dealership determines the eligibility of the vehicle owner to receive a treatment. If the vehicle owner is eligible, the method proceeds to step 725, at which point the dealership provides the vehicle owner with a new treatment of the TiO2 solution. At step 730, the dealership re-certifies that the vehicle has been treated with the TiO2 solution. At step 735, the dealership generates and transmits to the surety notice that of a claim under the surety contract. At step 736, the claim is either accepted or denied.

Returning to step 716, if the vehicle owner cancels the contract with the dealership, the method proceeds to step 740. At step 740, the surety determines a refund amount R or a cancellation penalty. In one embodiment, R is calculated by subtracting the per-treatment amount A (calculated in step 435) multiplied by n, the number of times that the vehicle has been treated already, from X, the total contract price. In a preferred embodiment:

$$R=X-(Y+(An)) \qquad \text{Eq. 2}$$

where:
R=refund amount or calculated penalty
A=per-treatment amount
X=total contract price
Y=dealer cost At step 745, the dealership refunds R to the vehicle owner. At step 750, the dealership generates and transmits to the surety notice that of a claim under the surety contract. At step 751, the claim is either accepted or denied.

Returning to step 716, if the contract between the dealership and the vehicle owner expires, then the method proceeds to step 755. At step 755, the dealership determines the expiration of the contract, and the method terminates.

Referring to FIG. 8, table 800 of chemical ingredients, by % weight, for a preferred embodiment of a TiO2 aqueous solution for use in the vehicle application. Chemical Abstracts Service numbers are included in the center column. The solution is prepared by combining the water and TiO2 and mixing thoroughly, allowing the TiO2 to evenly disperse in solution. Other chemical components are added in rapid succession thereafter, while mixing. In a preferred embodiment, DI water is provided at 100° F. and is maintained as this temperature during agitation. TiO2 should dissolve in solution. If not, agitation is continued, while the temperature is raised to 120° F., until a homogenous solution is achieved.

Figure 9:
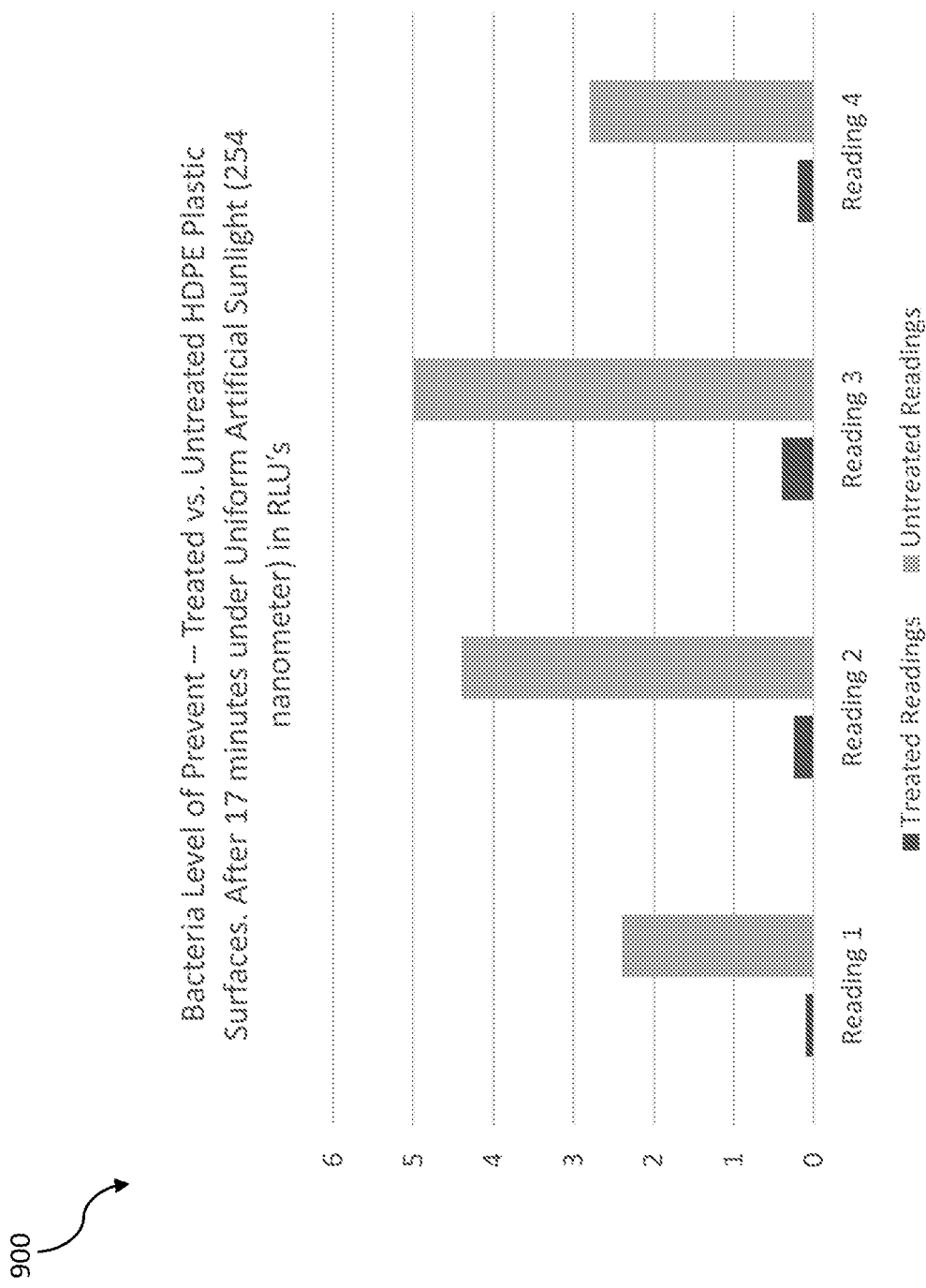
FIG. 9 is a graph of test results of bacteria level measurement data.

Referring to FIG. 9, graph 900 shows efficacy test measurement levels for multiple readings. The efficacy test measurements are performed on the vehicle before and then after the TiO2 application process. Tests can be done on the same surface or on a number of surfaces. However, the surface(s) tested must be the same from test to test. For example, initial reading 1 is performed when the vehicle is new. Readings 2, 3, and 4 are performed on the one year anniversaries when the vehicle is returned for re-application. In a preferred embodiment, the process settings and parameters are changed based on changes in measured bacterial infestation from test to test. The process parameters include the TiO2 solution formulation, the application pressure, and the curing time. The measurements are performed using relative light units (RLUs), which measure the amount of adenosine triphosphate (ATP) present on the surface. Adenosine triphosphate is used by organisms and organic matter as a unit of energy so that elevated levels of adenosine triphosphate indicate an increased likelihood of the presence of bacteria. In an example set of tests, reading 1 shows the before treatment value of 2.4 RLUs and an after treatment value of 0.1 RLUs. Reading 2 shows a before treatment RLU value of 4.4 and after treatment value of 0.025 RLUs. Reading 3 indicates a before treatment value of RLUs and an after treatment value of 0.4 RLUs. Reading 4 shows a before treatment value of 2.8 RLUs and an after treatment value of 0.2 RLUs.

Figure 10:
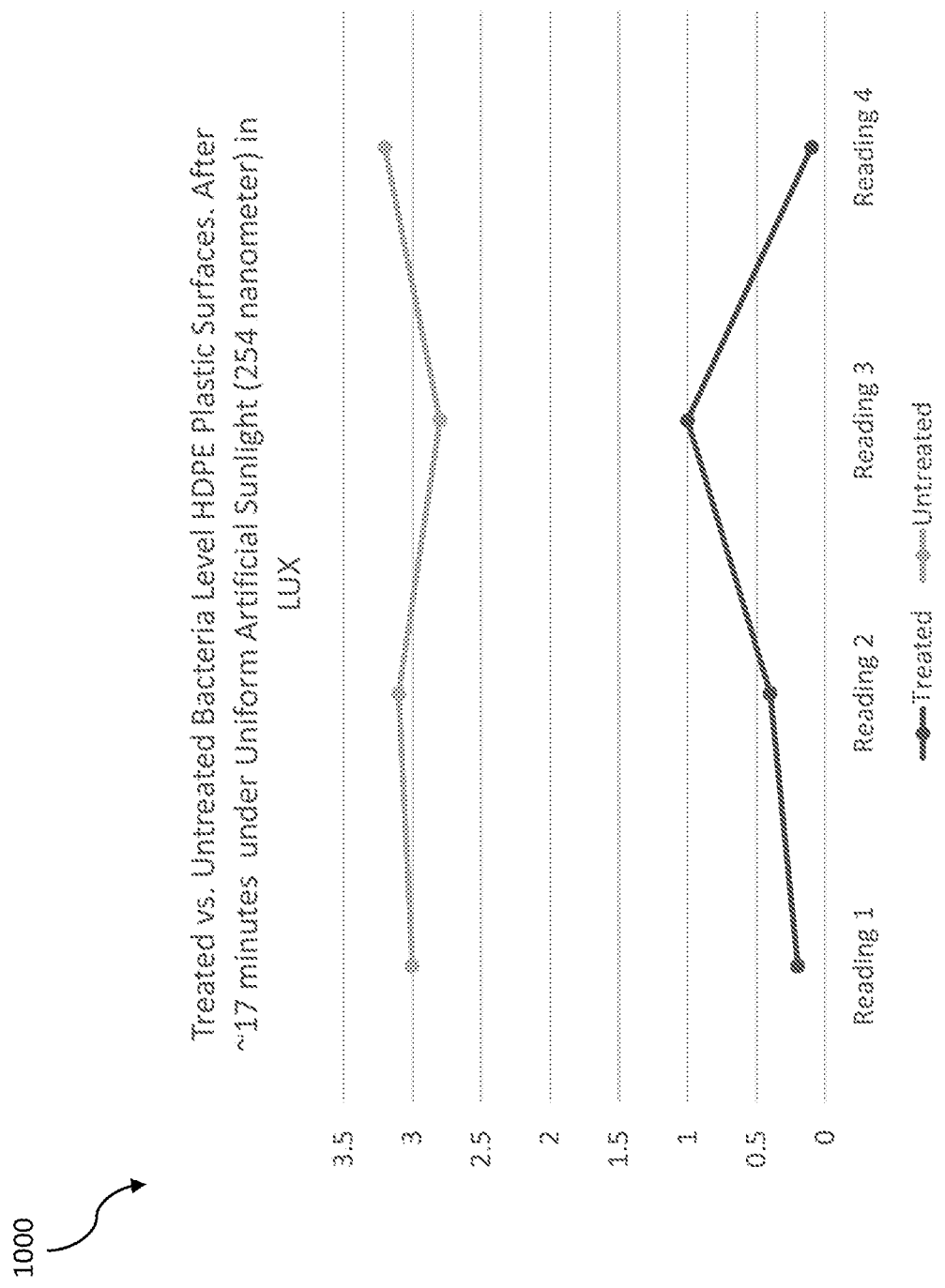
FIG. 10 is a graph of test results of bacteria level measurement data.

Referring to FIG. 10, graph 1000 shows bacterial levels. Graph 1000 may be provided by system 100 to user client device 104 with dealer server 140 after each time the vehicle is brought in treatment. In an example set of tests, the top line for untreated values had RLU measurements of 3, 3.1, 2.9, and 3.2 for readings 1 through 4. The bottom line shows after treatment readings 1 through 4 with RLU measurements of 0.2, 0.4, 1, and 0.1.

Figure 11:
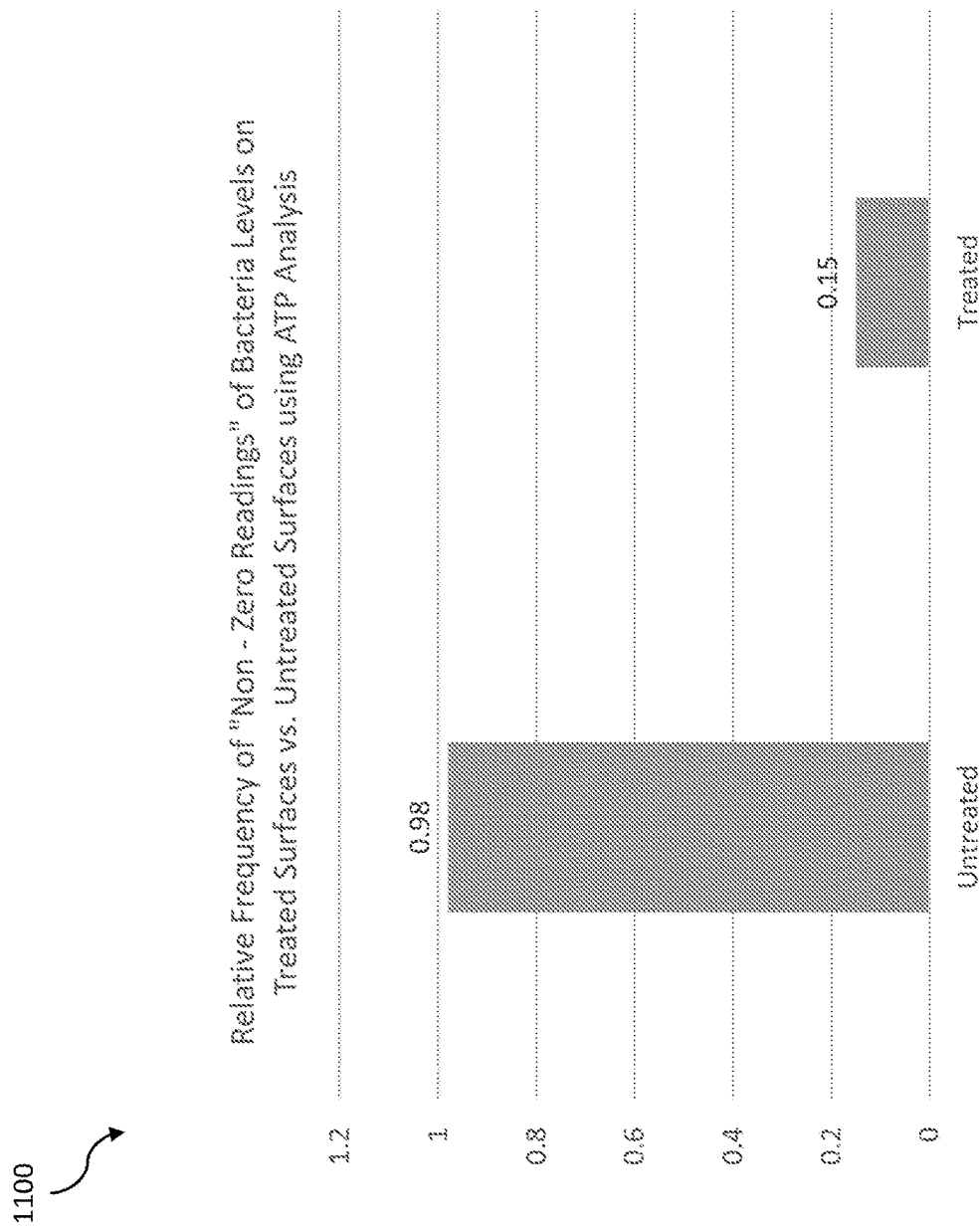
FIG. 11 is a graph of test results of bacteria eradication levels.

Referring to FIG. 11, graph 1100 shows bacteria eradication test results. In an example set of tests, the relative frequency of non-zero readings is at 0.98 for untreated surfaces and at 0.15 for treated surfaces.

Figure 12:
FIG. 12 is a table of chemical components for a preferred embodiment of an aqueous solution of TiO2.

Referring to FIG. 12, table 1200 of chemical ingredients, by % weight, for another preferred embodiment of a TiO2 aqueous solution for use in the vehicle application. The aqueous solution employs an anatase doped TiO2 in the range of about 1.50% to about 15.00%. The introduction of doping agents during the generation of the TiO2 changes the crystalline structure and allows the TiO2 to absorb light over a broader light spectrum. This increases the photocatalytic effects of the TiO2 when exposed to light with longer wavelengths, such as interior lights. Absorption of light at longer wavelengths decreases the need for exposure to light with UV wavelengths to obtain the maximum disinfecting benefits of the TiO2.

The doping compositions may preferably be drawn from the group consisting of silver, zinc, silicon, carbon, nitrogen, sulfur, iron, molybdenum, ruthenium, copper, osmium, rhenium, rhodium, tin, platinum, lithium, sodium, and potassium and combinations thereof. Particularly preferred doping agents are zinc, silver, silicon, and copper or combinations thereof. Zinc, silver, and copper have disinfectant and antimicrobial characteristics which can work in combination with the disinfectant qualities of the TiO2.

In a preferred embodiment, 2-amino-2-ethyl-1,3 propanediol is included at about 0.10% to about 1.00% for increased solution stability and dispersion. Thymol is included at about 0.3% to about 1.00% as an additional disinfectant. Fragrances is included at about 0.001% to about 0.30%. Fragrances can be from multiple natural fragrances or essential oils including but not limited to anise, basil, cedar, cinnamon, citron, eucalyptus, frankincense, geranium, grapefruit, jasmine, lavender, lemon, lime, mandarin, mint, nutmeg, orange, peppermint, pine, rose, spearmint, tangerine, and wintergreen and combinations thereof. A preferred fragrance is clean kitchen lemon from International Aromatics, Inc. sold under product code 07-18-79391. The remainder of the aqueous solution is deionized water.

In a preferred embodiment, the fragrance for the aqueous solution can be selected per customer preference or request.

As used herein, the term "about" means±0.5%.

The invention claimed is:

1. A method for chemically disinfecting an interior of a vehicle comprising:
providing a chemical composition comprising anatase doped $TiO_2$, thymol, and deionized water;

applying the chemical composition to the interior of the vehicle in an airborne suspension;
sealing the vehicle;
curing the chemical composition; and,
wiping the interior of the vehicle.

2. The method of claim 1 further comprising:
providing 2-amino-2-ethyl-1,3 propanediol to the chemical composition.

3. The method of claim 2 wherein the step of curing further comprises exposing the chemical composition to ultraviolet light.

4. The method of claim 3 wherein the step of exposing further comprises exposing the chemical composition to ultraviolet light in a range of about 320 nm to about 395 nm.

5. The method of claim 1 wherein the step of providing further comprises:
providing the chemical composition with a formula:

| | |
|---|---|
| anatase doped $TiO_2$ | about 3.00% to about 10.00% |
| 2-amino-2-ethyl-1,3 propanediol | about 0.10% to about 0.30% |
| thymol | about 0.40% to about 0.65% |
| fragrance | about 0.001% to about 0.10% |
| deionized water | about 88.85% to about 96.50%. |

6. The method of claim 1 wherein the step of providing further comprises:
providing the chemical composition with a formula:

| | |
|---|---|
| anatase doped $TiO_2$ | about 5.00% to about 6.00% |
| 2-amino-2-ethyl-1,3 propanediol | about 0.18% to about 0.20% |
| thymol | about 0.51% to about 0.55% |
| fragrance | about 0.001% to about 0.01% |
| deionized water | about 93.45% to about 95.61%. |

7. The method of claim 1 wherein the step of providing the chemical composition further comprises providing the anatase doped $TiO_2$ is doped with one of a group of zinc, silver, copper, silicone, and combinations thereof.

8. The method of claim 1 wherein the step of applying further comprises:
applying the chemical composition with one of a group of a spray bottle, an aerosol can, and a spray can.

9. The method of claim 1 wherein the step of applying further comprises:
applying the chemical composition with a fogger.

\* \* \* \* \*